US012558188B2

(12) United States Patent
Sancho Durá et al.

(10) Patent No.: US 12,558,188 B2
(45) Date of Patent: Feb. 24, 2026

(54) SYSTEMS AND METHODS FOR OPTICAL ANALYSIS AND CONTACT STABILITY USING ABLATION CATHETERS

(71) Applicant: Medlumics S.L., Madrid (ES)

(72) Inventors: Juan Sancho Durá, Camaleño (ES); David Herranz Aragoncillo, Alpedrete (ES); Christophe Bailleul, Paris (FR); James L. Greene, Shelfield Green (GB); Matthieu Duperron, Madrid (ES); Abel Roigé, Alcobendas (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 18/392,268

(22) Filed: Dec. 21, 2023

(65) Prior Publication Data

US 2024/0207013 A1     Jun. 27, 2024

(30) Foreign Application Priority Data

Dec. 22, 2022    (EP) .................................... 22383258

(51) Int. Cl.
    *A61B 90/00*        (2016.01)
    *A61B 5/00*         (2006.01)
                        (Continued)
(52) U.S. Cl.
    CPC ............ *A61B 90/37* (2016.02); *A61B 5/0066* (2013.01); *A61B 5/0084* (2013.01);
                        (Continued)
(58) Field of Classification Search
    CPC .................................................... A61B 90/37
    See application file for complete search history.

(56) References Cited

U.S. PATENT DOCUMENTS

2008/0275428 A1    11/2008   Tegg et al.
2021/0212569 A1    7/2021    Sancho Duráet al.

FOREIGN PATENT DOCUMENTS

WO        2016020525 A2      2/2016

OTHER PUBLICATIONS

Stabile, Giuseppe et al., "Catheter-Tissue Contact Force Values Do Not Impact Mid-Term Clinical Outcome Following Pulmonary Vein Isolation in Patients With Paroxysmal Atrial Fibrillation," J. Interventional Cardiology Electrophysiology, Nov. 2014; 7 pages.
(Continued)

*Primary Examiner* — Joseph M Santos Rodriguez
(74) *Attorney, Agent, or Firm* — Sterne, Kessler, Goldstein & Fox P.L.L.C.

(57)        ABSTRACT

Described herein are systems and methods for performing optical signal analysis for tissue ablation using a catheter having viewports. A method includes transmitting illumination toward a target tissue via the viewport. The method also includes receiving, at a first viewport, a first scattered illumination from the target tissue and generating a first measurement signal based on the first scattered illumination. The method also includes receiving, at the first viewport, a second scattered illumination from the target tissue after the receiving of the first scattered illumination and generating a second measurement signal based on the second scattered illumination. The method also includes determining whether the viewport is in contact with the target tissue based on a first difference among the plurality of optical measurements meeting or crossing a first threshold value, wherein the first difference comprises a difference between the first and second measurement signals.

20 Claims, 11 Drawing Sheets

(51) Int. Cl.
     A61B 18/14          (2006.01)
     A61B 34/10          (2016.01)
     *A61B 18/00*          (2006.01)
     *A61B 34/00*          (2016.01)

(52) U.S. Cl.
     CPC .......... *A61B 5/6885* (2013.01); *A61B 5/6886*
            (2013.01); *A61B 18/1492* (2013.01); *A61B*
        *34/10* (2016.02); *A61B 2018/00351* (2013.01);
         *A61B 2018/00577* (2013.01); *A61B 2034/104*
           (2016.02); *A61B 34/25* (2016.02); *A61B*
                  *2090/373* (2016.02)

(56)           References Cited

OTHER PUBLICATIONS

Virk, Sohaib A. et al., "Updated Systematic Review and Meta-Analysis of the Impact of Contact Force Sensing On the Safety and Efficacy of Atrial Fibrillation Ablation: Discrepancy Between Observational Studies and Randomized Control Trial Data," European Society of Cardiology, Europace, vol. 21, 2019; pp. 239-249.

300

310

325

316

320

312

314

330

302

304

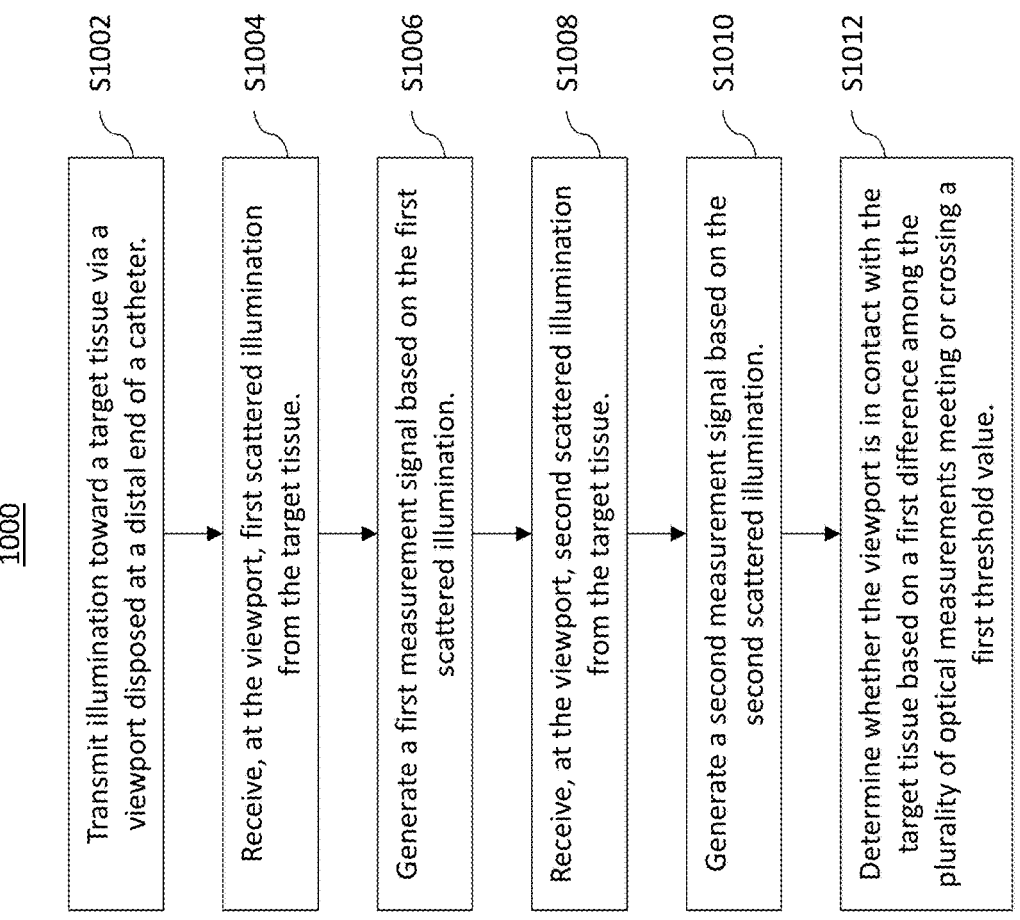

1000

S1002

Transmit illumination toward a target tissue via a viewport disposed at a distal end of a catheter.

S1004

Receive, at the viewport, first scattered illumination from the target tissue.

S1006

Generate a first measurement signal based on the first scattered illumination.

S1008

Receive, at the viewport, second scattered illumination from the target tissue.

S1010

Generate a second measurement signal based on the second scattered illumination.

S1012

Determine whether the viewport is in contact with the target tissue based on a first difference among the plurality of optical measurements meeting or crossing a first threshold value.

FIG. 10

SYSTEMS AND METHODS FOR OPTICAL ANALYSIS AND CONTACT STABILITY USING ABLATION CATHETERS

CROSS-REFERENCE TO RELATED APPLICATIONS

This application claims priority to European Patent Application No. 22383258.5, filed on Dec. 22, 2022, which is incorporated herein by reference in its entirety.

BACKGROUND

Field

Aspects of the present disclosure relate to components, systems, and methods performing tissue ablations. Examples implementations may include optical signal analysis, predicting lesion depths for tissue ablations, and determining stability of contact between a catheter tip and a tissue sample.

Background

Ablation is a medical technique for producing tissue necrosis. It is used to help treat different pathologies including cancer, Barret's esophagus, or cardiac arrhythmias, among others. For radiofrequency (RF) ablation, the application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen, myosin, or elastin. Traditionally, RF ablation is done by placing an external electrode on the patient's body, and applying an alternating potential to the tip of a catheter that is placed in contact with the tissue to be treated within the patient's body.

In some cases, various energy sources may be utilized for ablation, including cryogenic cooling for cryoablation, radiofrequency, microwave, laser, photoacoustic, ultrasound, pulsed field, or the like. In some cases, cryoablation may use extremely cold temperatures for ablating tissue, whereas electroporation ablation may use pulsed electric fields to ablate specific tissue for the treatment of atrial fibrillation.

The ablation effect depends on a number of factors, including applied electrical power, quality of the electrical contact, local tissue properties, presence of blood flow close to the tissue surface, and the effect of irrigation. Because of the variability of these parameters, it may be difficult to obtain consistent results and understand ablation effects in tissue using current systems and methods for ablation.

Accordingly, such systems and methods may be limited because of the difficulties and challenges in assessing the results of ablation in tissue, such as identifying a lesion formed in the tissue and determining various properties of the lesion through the catheter. Ablation may be paired with optical instruments to inspect the ablated tissue (e.g., using optical coherence tomography). The quality of contact between the optical instrument and the target tissue may play affect the accuracy of the optical measurements.

BRIEF SUMMARY

Accordingly, disclosed herein are improved methods and/ or devices for assessing the quality of contact between the catheter tip and the target tissue.

One or more aspects of embodiments disclosed herein may be directed to optical systems, consoles or processing devices, catheters, and optical measurements for understanding optical properties (e.g., birefringence, polarization, and/or phase retardation of tissue) in order to monitor changes in the optical properties over time and predict lesion depths in the tissue.

In some aspects, a method may comprise performing a plurality of optical measurements of a target tissue via a viewport disposed at a distal portion of a catheter. The performing of the plurality of optical measurements may comprise transmitting illumination toward a target tissue via the viewport. The performing of the plurality of optical measurements may further comprise receiving, at the viewport, first scattered illumination from the target tissue. The performing of the plurality of optical measurements may further comprise generating a first measurement signal based on the first scattered illumination. The performing of the plurality of optical measurements may further comprise receiving, at the viewport, second scattered illumination from the target tissue after the receiving of the first scattered illumination. The performing of the plurality of optical measurements may further comprise generating a second measurement signal based on the second scattered illumination. The method may further comprise analyzing the plurality of optical measurements. The analyzing may comprise determining whether the viewport is in contact with the target tissue based on a first difference among the plurality of optical measurements meeting or crossing a first threshold value. The first difference may comprise a difference between the first and second measurement signals.

In some aspects, a system may comprise a catheter comprising a proximal portion a distal portion, a sheath, and a plurality of viewports. The sheath may be coupled between the proximal section and the distal section. A plurality of viewports may be disposed at the distal portion and are configured to transmit illumination to a target tissue and to receive scattered illumination from the target tissue. The system may further comprise a detection system configured to receive, via a first viewport of the plurality of viewports, first and second scattered illumination from the target tissue and to generate first and second measurement signals respectively based on the first and second scattered illumination. The system may further comprise a processing device configured to determine whether the first viewport is in contact with the target tissue based on a first difference between the first and second measurement signals meeting or crossing a first threshold value.

Further features of various aspects are described in detail below with reference to the accompanying drawings. It is noted that the specific aspects described herein are not intended to be limiting. Such aspects are presented herein for illustrative purposes only. Additional aspects will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

FIG. 10 shows a flowchart of a method, according to some aspects.

Aspects of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements may be used without departing from the spirit and scope of the present disclosure. It will be apparent to a person skilled in the pertinent art that this disclosure may also be employed in a variety of other applications.

It is noted that references in the specification to "one aspect," "an aspect," "an example aspect," "some aspects," or the like, indicate that the aspect(s) described may include a particular feature, structure, or characteristic, but every aspect may not necessarily include the particular feature, structure, or characteristic. Moreover, such phrases do not necessarily refer to the same aspect. Further, when a particular feature, structure or characteristic is described in connection with an aspect, it would be within the knowledge of one skilled in the art to effect such feature, structure or characteristic in connection with other aspects whether or not explicitly described.

It should be noted that although this application may refer specifically to cardiac ablation, the aspects described herein may target other pathologies as well, along with additional energy sources for ablation, including but not limited to cryogenic, RF, microwave, laser, ultrasound, and pulsed electric fields. The principles of using energy to treat other pathologies are similar, and therefore the techniques used to apply the energy are similar.

Herein, the terms "electromagnetic radiation," "light," "beam of radiation," "illumination," or the like, may be used to describe electromagnetic signals propagating through the various described elements and systems.

Example Catheter

Figure 1:
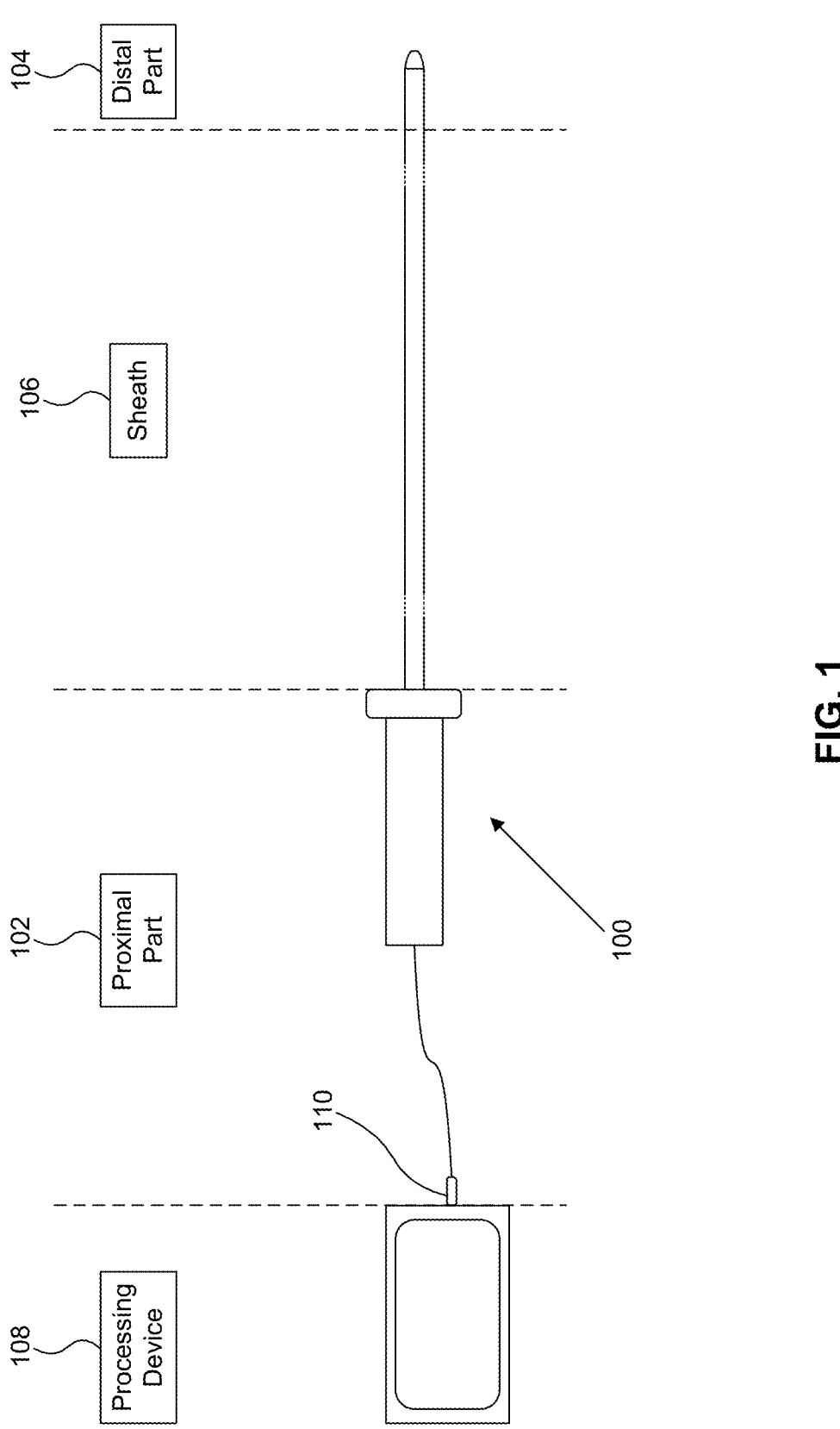
FIG. 1 shows a catheter, according to some aspects.

FIG. 1 shows a catheter 100, according to some aspects. In some aspects, catheter 100 may comprise a proximal section 102 (or proximal part), a distal section 104 (or distal part), and a sheath 106 coupled between proximal section 102 and distal section 104. Terms such as "section," "portion," "part," "component," or the like, may be used herein to describe a specific/smaller section of a larger structure (e.g., distal section of a catheter), a fraction of a whole (e.g., a portion of radiation), or the like. Sheath 106 may comprise one or more radiopaque markers for navigation purposes. Catheter 100 may further comprise a communication interface 110 between catheter 100 and a processing device 108. Communication interface 110 may comprise one or more optical fibers and connectors between processing device 108 and catheter 100. Communication interface 110 may further comprise an interface component, for example, a component for wireless communication, such as Bluetooth, WiFi, cellular, and the like, to communicate with the catheter 100 or other processing components in a catheter system.

In some aspects, sheath 106 and distal section 104 may be disposable. Proximal section 102 may be reused by attaching a new sheath 106 and distal section 104 each time a new procedure is performed. In some aspects, proximal section 102 may also be disposable.

In some aspects, proximal section 102 may house various electrical and optical components used in the operation of catheter 100. A first optical source may be included within proximal section 102 to generate a source beam of radiation. The source radiation may be used for optical evaluation of a sample tissue. Terms such as "sample," "tissue," "target tissue," or the like may be used herein to refer to a sample (e.g., a tissue sample) that is the target of an ablation and/or optical inspection process. The first optical source may comprise one or more laser diodes or light emitting diodes (LEDs). In a non-limiting example, the beam of radiation generated by the optical source may have a wavelength within the infrared range. In a non-limiting example, the beam of radiation may have a central wavelength of 1.3 μm. The optical source may be designed to output a beam of radiation at only a single wavelength, or it may be a swept source for outputting a range of different wavelengths.

In some aspects, the generated beam of radiation may be guided towards distal section 104 via the optical transmission medium connected between proximal section 102 and distal section 104 within sheath 106. Some examples of optical transmission media include single mode optical fibers and/or multimode optical fibers. In some aspects, the electrical transmission medium and the optical transmission medium are provided by the same hybrid medium allowing for both electrical and optical signal propagation.

In some aspects, proximal section 102 may comprise a second optical source, such as a laser energy source, to generate laser energy that is applied at distal section 104 for tissue ablation. The laser energy source may emit an ablation beam of laser energy at a wavelength of 980 nm or a wavelength of 1060 nm. The laser energy from the source in proximal section 102 may propagate down catheter 100 via an optical transmission medium connected between proximal section 102 and distal section 104 within sheath 106. The laser energy may be output from distal section 104 of catheter 100 to a target tissue, thereby ablating the target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 50 W that is applied to target tissue for 60-90 seconds.

In some aspects, processing device 108 may comprise one or more components, such as detectors, electronics, and/or other components of an optical circuit/system as described herein. The one or more components (e.g., detectors, electronics, and/or other components of an optical circuit/system) may be included in proximal section 102.

In some aspects, the example of laser ablation described above is not to be interpreted as limiting. Other ablation techniques have been described herein and are envisaged implementations of some aspects. One non-limiting example is pulsed field ablation (PFA). Those skilled in the art will appreciate that aspects of catheters described herein may comprise the hardware for delivering ablation energy according to the type of ablation being implemented.

In some aspects, proximal section 102 may comprise one or more components of an interferometer in order to perform low-coherence interferometry (LCI) using the light generated from the second optical source. Due to the nature of interferometric data analysis, the optical transmission medium used for guiding the light to and from distal section 104 may not affect the state and degree of light polarization. In some aspects, the optical transmission medium may affect the polarization in a constant and reversible way. In some aspects, proximal section 102 may further comprise interface elements with which a user of catheter 100 may use to control the operation of catheter 100. For example, proximal section 102 may comprise a deflection control mechanism that controls a deflection angle of distal section 104. The deflection control mechanism may be activated by a mechanical movement of an element on proximal section 102, or the deflection control mechanism may use electrical connections to control the movement of distal section 104. Proximal section 102 may comprise various buttons or switches that allow a user to control when laser energy is applied at distal section 104, or when the beams of radiation are transmitted from distal section 104, allowing for the acquisition of optical data.

In some aspects, proximal section 102 may comprise a deflection control mechanism for controlling one or more pull wires that are coupled to the distal section 104. The deflection control mechanism and the one or more pull wires may allow for steering of the distal section of catheter 100 in order to maneuver and target specific tissue regions for ablation.

In some aspects, distal section 104 may comprise a plurality of optical view ports (e.g., orifices). One or more of the optical view ports may be machined into the outer body of distal section 104. The optical view ports may be distributed over the outside of distal section 104, resulting in a plurality of distinct viewing directions.

In some aspects, the optical view ports may transmit and collect light (e.g., optical signals) at various angles from the distal section 104. The optical view ports also allow for a plurality of directions (e.g., beam directions) in which laser energy may be directed for tissue ablation through one or more of the optical view ports. Each of the plurality of viewing directions may be substantially non-coplanar. The optical view ports may also be designed with irrigation functionality to cool distal section 104 and surrounding tissue during ablation.

Figure 2A:
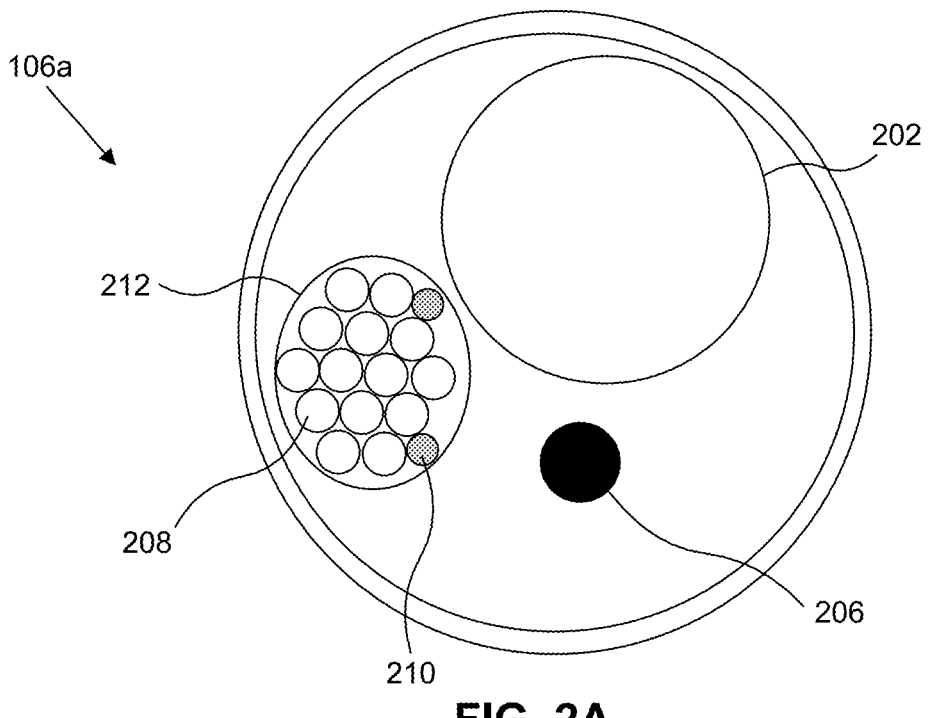
FIGS. 2A and 2B show cross sections of a catheter, according to some aspects.
Figure 2B:
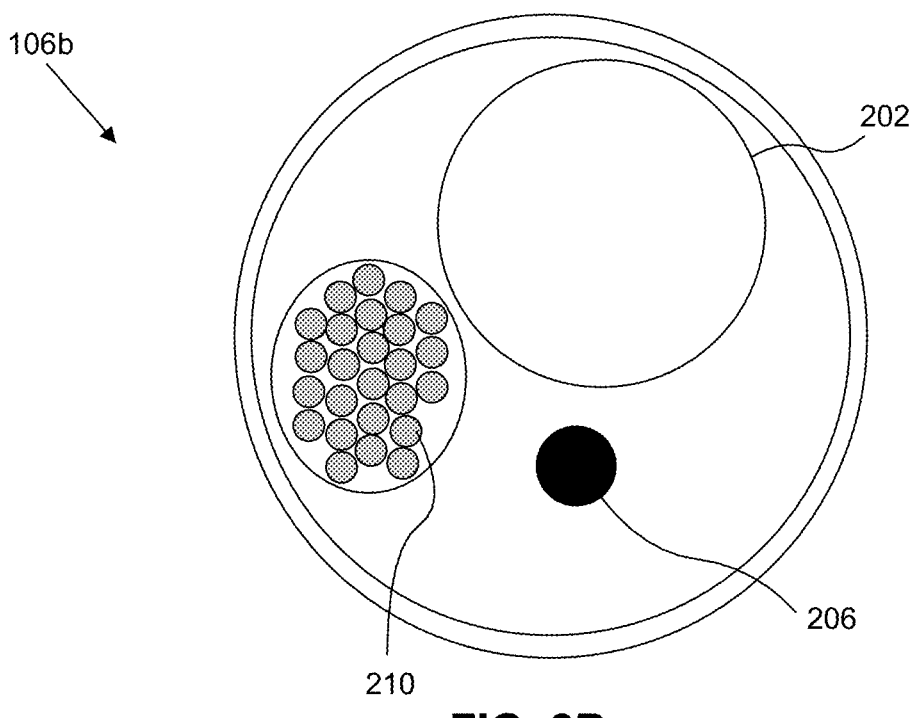

FIGS. 2A and 2B show cross-sections of sheath 106, according to some aspects. Sheath 106 may comprise all of the elements interconnecting proximal section 102 with distal section 104. Sheath 106a illustrates an aspect that houses an irrigation channel 202, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal section 104.

In some aspects, optical transmission media 210 and other components may be located within a protective cover that is separate from the protective cover 212 in which the electrical connections 208 is housed. One or more of optical transmission media 210 may guide light generated from the optical source (exposure light) towards distal section 104. In some aspects, another subset of optical transmission media 210 may guide light returning from distal section 104 (scattered or reflected light) back to proximal section 102. In another example, the same one or more optical transmission media 210 guides light in both directions. In some aspects, the optical transmission medium 210 may comprise one or more single mode optical fibers, one or more multimode optical fibers, or a combination of single mode and multimode optical fibers.

In some aspects, irrigation channel 202 may be a hollow tube used to guide cooling fluid towards distal section 104. Irrigation channel 202 may comprise heating and/or cooling elements disposed along the channel to affect the temperature of the fluid. Irrigation channel 202 may also be used for suctioning or drawing fluid surrounding distal section 104 back towards proximal section 102.

In some aspects, deflection mechanism 206 may comprise electrical or mechanical elements designed to provide a signal to distal section 104 in order to change a deflection angle of distal section 104. The deflection system may allow guidance of distal section 104 by actuating a mechanical control placed in proximal section 102. This system may be based on a series of aligned and uniformly spaced cutouts in sheath 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other aspects involving the combination of several control wires attached to the catheter tip may allow the deflection of the catheter tip along different directions.

FIG. 2B illustrates a cross-section of sheath 106b. Sheath 106b depicts an aspect having most of the same elements as sheath 106a from FIG. 2A, except that there are no electrical connections 208. Sheath 106b may be used in situations where modulation (e.g., multiplexing) of the generated beam of radiation is performed in proximal section 102. In some aspects, sheath 106b may be implemented in a diagnostic catheter that is used for laser or cryogenic ablation.

Example Catheter System

Disclosed herein are aspects of an ablation catheter and console system that may use optical coherence tomography (OCT) and/or optical coherence reflectometry (OCR), refractometry, or other methods to perform tissue ablations, track scar formation in real-time, and monitor/verify lesion geometries and isolation by directly observing the scar pattern in tissue. To assess if a scar is formed, the methods, devices, and systems described herein may acquire optically reflected/refracted light from the tissue, determine optical properties of the reflected light (e.g., by measuring intensity and polarization and computing phase retardation and/or birefringence of tissue based on the measurements), and monitor changes, as these optical properties change when tissue is scarred when compared to healthy tissue. By identifying the changes in optical properties of the tissue, lesion depths and denaturation times in tissue may be predicted for various ablation times, as described herein.

Figure 3:
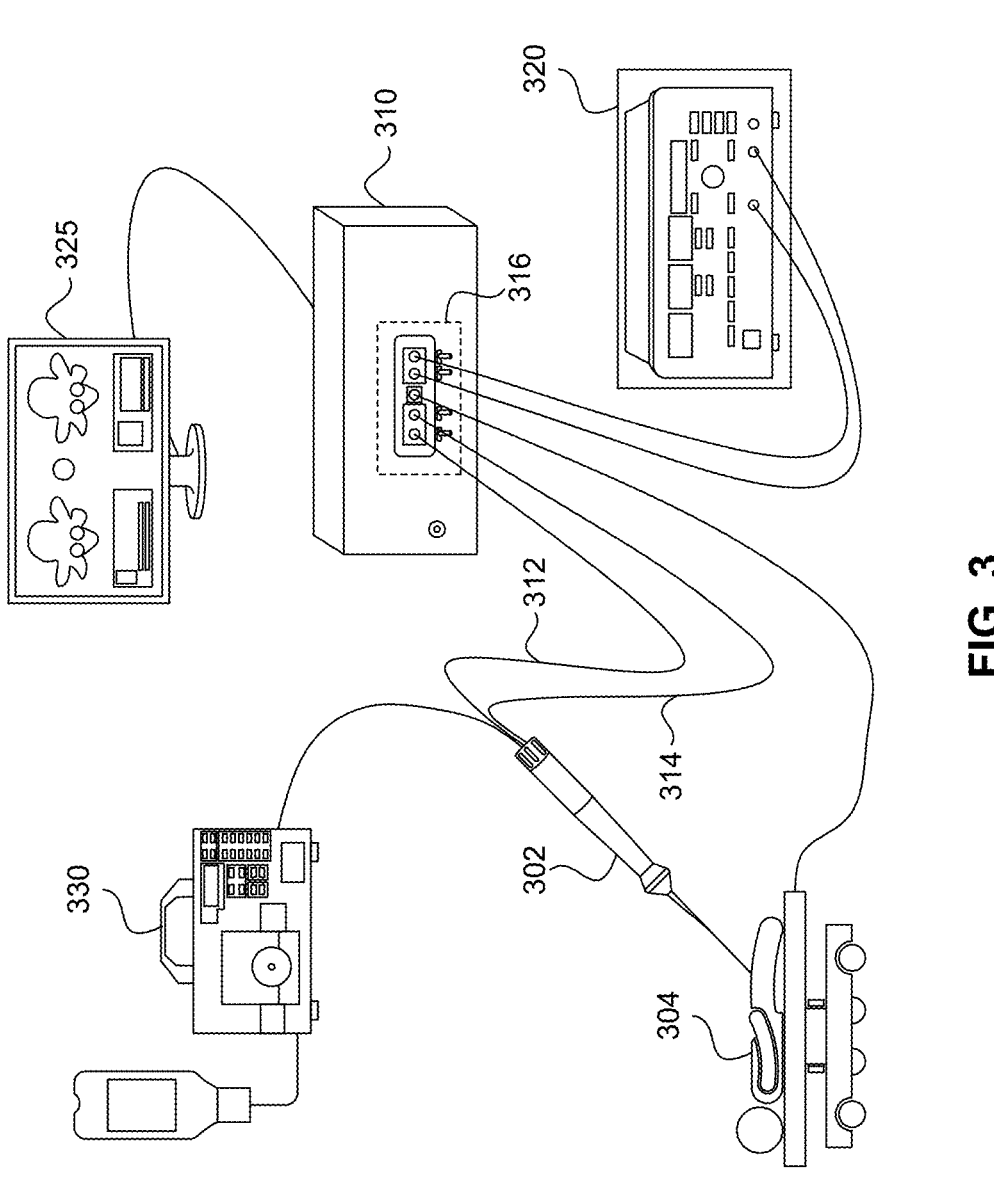
FIG. 3 shows a system for ablation and lesion prediction, according some aspects.

FIG. 3 shows a system 300 for performing ablation and lesion prediction, according to some aspects. In some aspects, system 300 may comprise catheter 302, console 310, signal generator 320, display 325, and irrigation pump 330. Catheter 302, console 310, signal generator 320, display 325, and irrigation pump 330 may be communicatively coupled together via wired and/or wireless connections. Catheter 302 may represent one or more aspects of catheter 100 shown in FIG. 1. A distal section of catheter 302 may be positioned at a portion of tissue in patient 304. It is understood that some aspects described herein may be implemented in vivo and/or in vitro.

In some aspects, catheter 302 may be positioned at a portion of tissue subject to ablation using energy generated by signal generator 320. Signal generator 320 may be an electronic device configured to generate radiofrequency (RF), cryogenic, or electroporation (e.g., pulsed electric field) signals for ablation. Signal generator 320 may be coupled to catheter 302 (e.g., via the console 310). Signal generator 320 may send energy to catheter 302 to ablate the portion of tissue at a selected tissue site.

In some aspects, the portion of tissue may comprise myocardial tissue, cardiac muscle tissue, skeletal tissue, or the like. Energy may be applied to the portion of tissue through optical view ports in the distal section of catheter 302. Structural changes in the tissue may be observed by acquiring optical signals via one or more optical view ports of catheter 302.

In some aspects, console 310 may comprise a computing device configured to acquire the optical signals from catheter 302 and analyze the optical signals to detect changes in optical properties of the tissue. Console 310 may include hardware (e.g., circuits), firmware, software, or any combination thereof to perform analysis of the optical signals and generate models for predicting lesion depths and ablation times as described herein.

In some aspects, console 310 may send light through an optical circuit within itself and the catheter 302 and into the tissue to monitor scar progression, contact between the tissue and catheter 302, and other characteristics of the tissue. Console 310 may be referred to herein as a control console, a processing device, and/or controller. Console 310 may be coupled to display 325, which may present results from the optical signal analysis and lesion predictions and allow a user to select/view, modify, and/or control parameters related to operation of catheter 302, console 310, signal generator 320, and/or irrigation pump 330. System 300 may implement a graphical user interface (GUI). The GUI may be displayed at display 325.

In some aspects, irrigation pump 330 may be coupled to catheter 302 via fluid conduit(s) (e.g., tubing). Irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation. Optical ports may also be cleared of obstruction in this manner.

In some aspects, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may comprise wiring, pins, and/or components used for supplying power and energy from signal generator 320 to catheter 302 for ablation.

In some aspects, the optical and electrical connections 312, 314 may be connected to console 310 via a communication interface 316. Communication interface 316 may allow for transmission of various signals (e.g., optical and electrical signals) between catheter 302 and console 310. Communication interface 316 may comprise a connector that facilitates proper alignment of optical fibers between the catheter 302 and console 310. In a non-limiting example, a pigtail connector may be used to connect optical fibers. In some aspects, the connector design may include both electrical and optical extension lines.

Example Optical System

Figure 4:
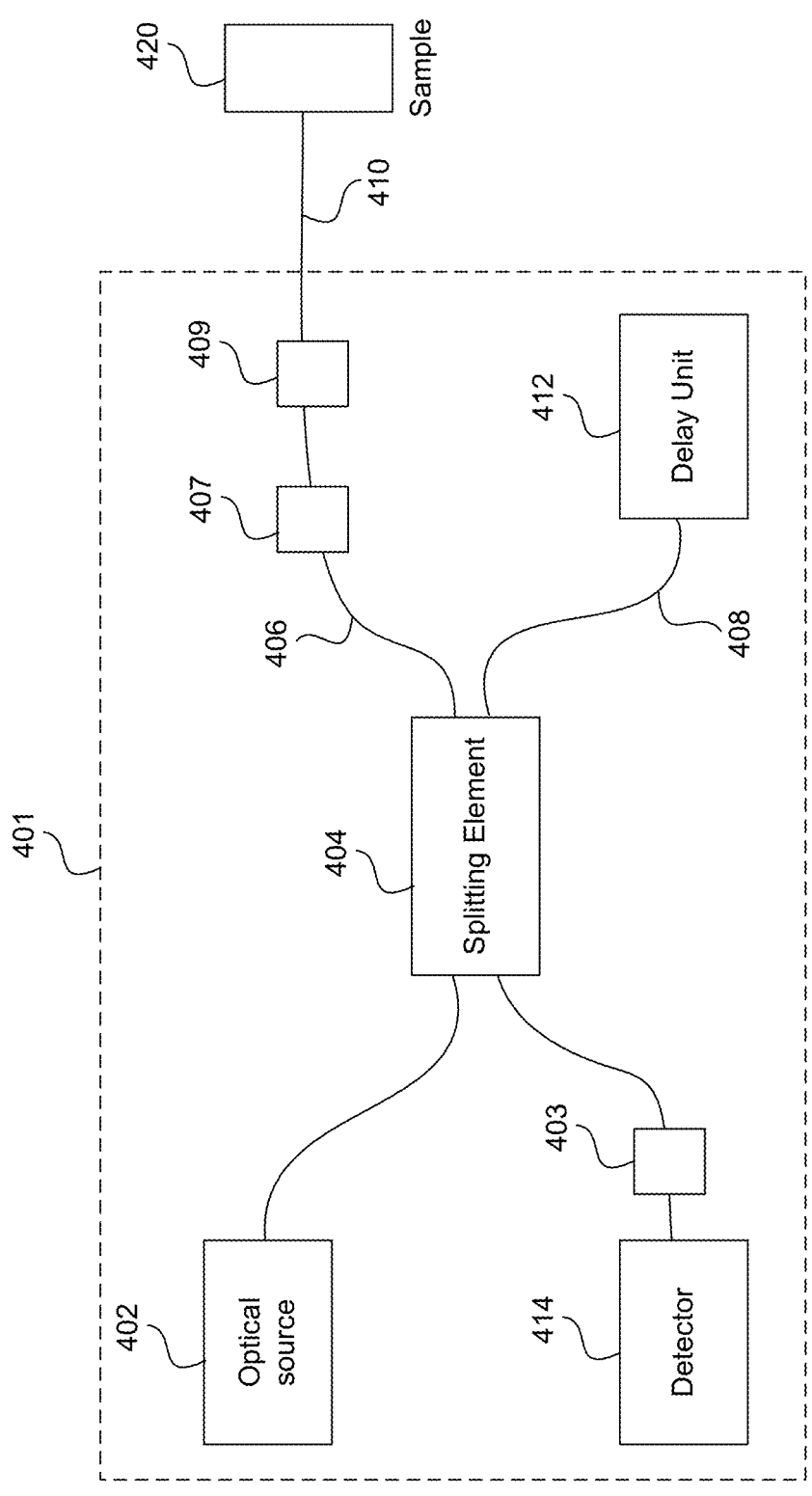
FIG. 4 shows an optical system for optical inspection of a sample, according to some aspects.

FIG. 4 shows an optical system 401 for imaging a sample 420, according to some aspects. In some aspects, components of optical system 401 may be implemented in console 310 to acquire optical measurements of the sample 420 using catheter 302. In some aspects, sample 420 may be a tissue surface of a patient's body.

In some aspects, optical system 401 may utilize low-coherence interferometry LCI, OCT, OCR, and/or or other optical modalities to perform optical inspections (e.g., imaging of tissue). Optical system 401 may comprise optical source 402, polarization splitter 403, coupling/splitting element 404, sample arm 406, polarization switch 407, reference arm 408, optical switch 409, output fibers 410, delay unit 412, and detection system 414. Those skilled in the art will appreciate that optical system 401 may comprise any number of other optical elements, some of which may not be explicitly shown for the sake of clarity. For example, optical system 401 may include mirrors, lenses, gratings, splitters, micromechanical elements, and/or the like, along the paths of sample arm 406 or reference arm 408.

In some aspects, optical source 402 may generate a source beam of radiation that is coupled to coupling/splitting element 404 via one or more fibers. Coupling/splitting element 404 may be used to direct light received from optical source 402 to both sample arm 406 and reference arm 408. Coupling/splitting element 404 may be, for example, a coupling element (e.g., a bi-directional coupler), an optical splitter, an adjustable splitting-ratio coupler, or any other modulating optical device that converts a single beam of light into two or more beams of light. The light from the optical source 402 may also go through an optical attenuator.

In some aspects, light that travels down sample arm 406 may impinge upon sample 420 by traveling through a polarization switch 407 and an optical switch 409. Polarization switch 407 may be included on the sample arm 406, but may also be at the input of the LCI system (e.g., prior to the splitting/coupling element 404). After passing through polarization switch 407, optical switch 409 may direct the light to one or more of the multiple output fibers 410. The multiple output fibers 410 may represent the fibers at the console 310 that are coupled to fibers of the catheter 302 via a connector.

In some aspects, sample 420 may be any suitable sample to be imaged, such as tissue. The light scatters and reflects back from various depths within sample 420 and the scattered/reflected radiation is collected back into sample arm 406. The scan depth may be chosen via the delay imposed on the light within delay unit 412.

In some aspects, a delay unit 412 may comprise various light-modulating elements. The light-modulating elements may perform phase and/or frequency modulation to counteract undesired optical effects in the light and/or to select one or more depths of sample 420 to be imaged. In some aspects, delay unit 412 may also control the light polarization of the reference arm and/or modulate the polarization. The modulation schemes on the reference arm 408 may simplify the need of a switching element in the reference arm and may allow forms of multiplexing other than time-multiplexing (e.g., frequency, phase, code, and/or polarization multiplexing).

In some aspects, delay unit 412 may be located within reference arm 408. However, it should be understood that delay unit 412 may instead be located in sample arm 406. Alternatively, various elements of delay unit 412 may be present in both sample arm 406 and reference arm 408. For example, elements of delay unit 412 that introduce a variable delay to the light may be located in sample arm 406, while elements that modulate different polarization modes of the light may be located in reference arm 408. In another example, elements of delay unit 412 that modulate different polarization modes of the light may be located in sample arm 406, while elements that introduce a variable delay to the light may be located in reference arm 408. In one example, sample arm 406 and reference arm 408 are optical fibers. Other implementations may be considered as well, such as, for example, fiber optic systems, free-space optical systems, photonic integrated circuits, and/or the like.

In some aspect, light may be coupled from optical source 402 to coupling/splitting element 404 via one or more fibers, and light may be coupled from splitting element 404 to polarization splitter 403 to detection system 414 via one or more fibers or by direct free-space coupling.

In some aspects, optical switch 409 may allow for selection of one or more beams through the multiple output fibers 410. In a non-limiting example, one beam may be active at a time, such that the signal coming back from the sample 420 may be combined with the reference arm 408 and then split into different channels in detection system 414 using a polarization splitter 403. This may allow birefringence and other optical properties of the tissue to be measured from one channel at a time. In other aspects, multiple beams may be active at the same time and split by a multiplexer or other type of beam splitter, in which each beam from each path may be discerned by their frequency, wavelength, amplitude, or other optical characteristics of light.

In some aspects, the light within sample arm 406 and reference arm 408 may be recombined by coupling/splitting element 404 (or by a different optical coupling element) and then split by polarization splitter 403 before being received at detection system 414. The light may be polarized prior to coupling by the coupling/splitting element 404. In some aspects, the light may be split in the reference arm 408. Detection system 414 may include any number of photo-diodes, charge-coupling devices, and/or CMOS structures to transduce the received light into an electrical signal. The electrical signal contains depth-resolved optical data related to sample 420 and may be received by a processing device for further analysis and signal processing procedures. As used herein, the term "depth-resolved" defines data in which one or more portions of the data related to specific depths of an imaged sample may be identified.

In some aspects, optical source 402, detection system 414, and delay unit 412 are located within proximal part 102 of catheter 100. Alternatively, optical source 402, detection system 414, and delay unit 412 may be located within processing device 108. Coupling/splitting element 404, polarization splitter 403, polarization switch 407, optical switch 409, and at least part of one or both of sample arm 406 and reference arm 408 may be located in processing device 108 or in either proximal part 102 or distal part 104 of catheter 100. Components of optical system 401 may be located in processing device 108 or in the console 310 of the catheter system 300 (FIG. 3).

In some aspects, detection system 414 may be located in a handle of the catheter 100, whereas and source 402 may be located in processing device 108. Optical source 402 may comprise one or more light emitting diodes (LEDs) or laser diodes. For example, LEDs may be used when performing time domain and/or spectral domain analysis, while tunable lasers may be used to sweep the wavelength of the light across a range of wavelengths. Components of optical system 401 may be located external to catheter 100 or catheter 302, for example, within processing device 108 or within console 310.

In some aspects, optical system 401 is illustrated as an interferometer design similar to a Michelson interferometer. However, other interferometer designs are possible as well, including Mach-Zehnder or Mireau interferometer designs. Components in optical system 401 may be adapted for a spectral-domain OCT configuration. For example, optical source 402 may be a super-luminescent diode (SLED) or light-emitting diode (LED), and detection system 414 may be a spectrometer in order to conduct optical spectroscopy of tissue.

Example Analysis of Optical Measurements

In some aspects, optical signals may be obtained by the catheter, and the optical system in the console may perform analysis of the optical signals and generate models for predicting lesion depths and ablation times as described herein. A predicted lesion depth may represent a height and a width of a lesion formed by the energy applied to a portion of tissue by a catheter.

Figure 5B:
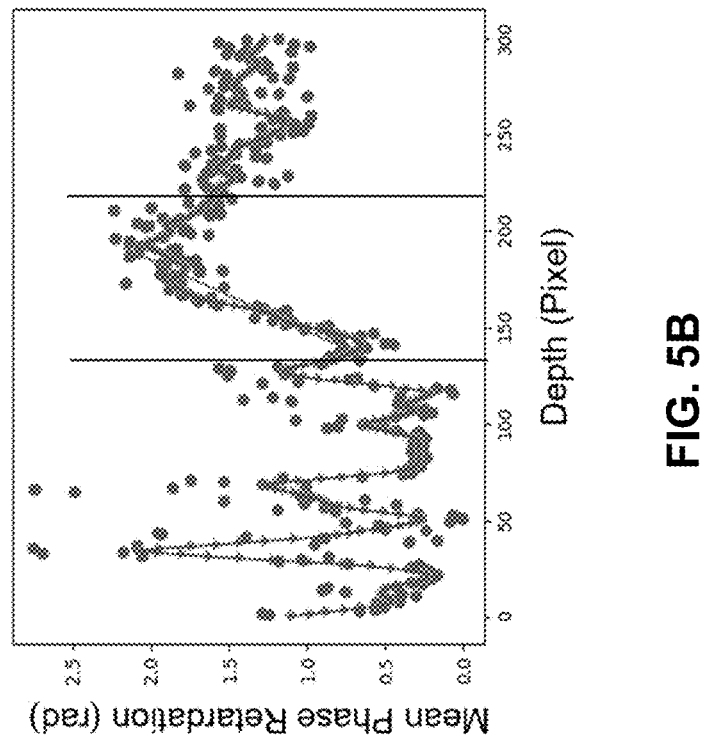
FIGS. 5A and 5B show plots of data from optical measurements of tissue, according to some aspects.
Figure 5A:
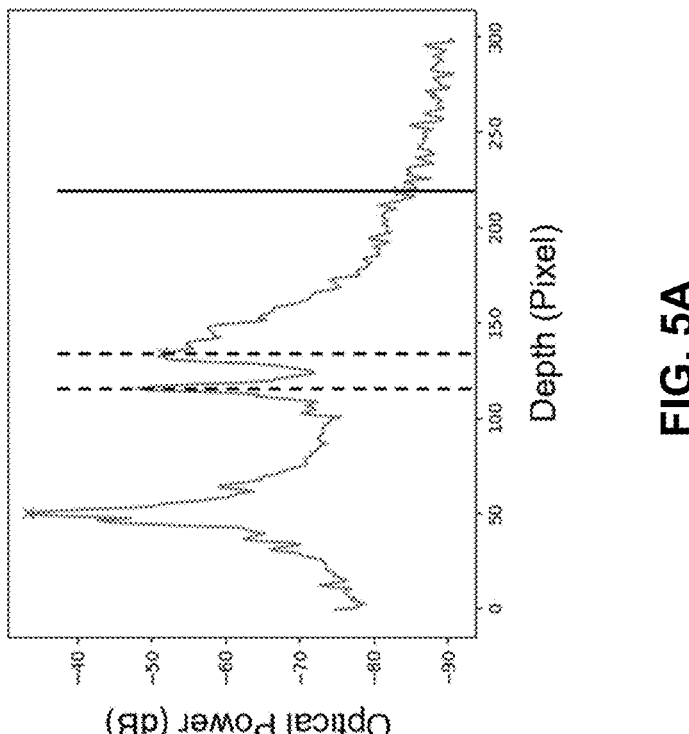

FIGS. 5A and 5B show plots of data from optical measurements of tissue, according to some aspects. To generate the data, an example study was conducted in order to develop a lesion depth prediction algorithm using optical property measurements from ablated tissue. In the study, tissue samples were excised from swine hearts, and a distal end of the catheter was perpendicularly positioned at the endocardial surface of the tissue using a micro-positioner. The tissue samples included right atrial free wall, superior vena cava, left atrial roof, mitral annulus, and left atrial appendage. To make the measurements, the catheter was suspended over the tissue from a spring to maintain constant contact force and reduce the effect of external mechanical vibrations on the contact force recordings. The micro-positioner was adjusted to achieve desired contact force values, and the force was measured using a weighing scale.

Some aspects of the present disclosure are directed to solving issues arising from traditional contact force measurements to achieve a catheter-to-tissue contact of a given quality. Some aspects disclosed herein are directed to using data from optical measurements to circumvent reliance on contact force sensors. Therefore, it is instructive to describe features and markers found in data from optical measurements, such as those illustrated in FIGS. 5A and 5B. For additional context, it is also instructive to describe how contact force measurements played a role in the study of the tissue that generated the data for FIGS. 5A and 5B.

In some aspects, contact between the catheter and tissue may be analyzed by direct visualization (e.g., using optical system 401) and change of force on the scale. A contact force of 0 grams, 2 grams, or 10 grams or more may respectively indicate no contact, a soft contact, or a strong contact between the catheter and tissue. Positive distances measured by the micro-positioner may indicate that the tissue is not in contact with the catheter tip, whereas negative distances measured by the micro-positioner may indicate that the catheter tip has been introduced to the tissue.

In some aspects, RF energy from the catheter's distal end was applied to tissue samples with power at levels between 20 and 40 W and RF ablation times ranging between 5 and 45 seconds. Focal RF ablations were performed in both the right and left atriums under varying parameters (e.g., including various power values, times, irrigation flow rates, and catheter contact force values). Optical measurements of the tissue were obtained using interferometry, OCT, and/or OCR techniques in order identify optical parameters of interest for predicting lesion depths.

In some aspects, such optical measurements may be obtained by using the optical system 401 of FIG. 4 as described herein. The information acquired via optical measurements may be used to represent an image of the target tissue (e.g., a 2D or 3D image).

FIG. 5A illustrates a graph of data corresponding to an example structural image, according to some aspects. The structural image from the study was calculated as an average of so-called AM-scans in a temporal window of 5 seconds. In some aspects, optical power as a function of tissue depth may be analyzed from the optical measurements to further assess catheter tip (e.g., end of distal section of catheter) and tissue distance and optical signal quality at different locations in the tissue based on catheter irrigation flow rates and angle of incidence values (e.g., beam direction of beam exiting from one or more of the optical view ports in the distal section of the catheter).

In some aspects, the tissue surface may be detected. A lens and tissue interface distance may be evaluated based on a distance of the two peaks, as shown by the two vertical dashed lines in FIG. 5A. In some aspects, a maximum image depth (e.g., optical penetration in tissue) may be calculated as a function of the distance between the first tissue interface with respect to the depth when the optical power is 5 dB above the noise background, as indicated by the third vertical line (solid line) shown in FIG. 5A. A linear regression model, such as a locally estimated scatterplot smoothing (LOESS) curve fitting regression, may be applied to the data.

FIG. 5B illustrates a graph of example mean phase retardation that is calculated as an average of so-called A-scans of the structural image, according to some aspects. In some aspects, the phase retardation slope may correspond with the slope measured from the tissue interface (as indicated by the two vertical lines shown in FIG. 5B) with the maximum phase retardation.

In some aspects, the system (e.g., catheter system 300 and optical system 401) may measure intensity and polarization of radiation scattered by tissue, from which phase retardation data and tissue properties such as birefringence may be extracted. Structural changes in the tissue may be related to the A-scan and/or intensity measurements. Phase retardation data may provide information about the tissue, including information on lesion depths and structural changes in the tissue, such as necrosis and tissue denaturation. In particular, a heart wall comprises three layers: the outer epicardium, the middle myocardium, and the inner endocardium, in which the myocardium is the muscle tissue of the heart and is composed of cardiac muscle cells (cardiomyocytes). Cardiac muscle cells have highly organized cell structures with myofibrils and sarcomeres that are branch-like. Microscopically, the arrangement of sarcomeres and myofibrils in cardiac muscle result in a striated appearance.

In some aspects, untreated myocardial tissue that has not been ablated may have a high level of cellular organization, which exhibits a significant phase retardation (PR) between anti-parallel polarization states. A high level of cellular organization may lead to reflect polarized light with phase wrapping around $\pi$ over the accumulative phase retardation. In some aspects, phase retardation may accumulate as light travels deeper through myocardial tissue at a rate proportional to the magnitude of birefringence. Thus, less organization in the muscular structure of the cardiac muscle tissue may have a direct influence on the properties of tissue birefringence.

FIG. 5B shows the accumulated phase retardation at each depth with respect to the tissue surface between 0 and $\pi$ (phase wrapping). In some aspects, mean phase retardation may be calculated as an average of A-scans in a temporal window of 5 seconds. The information obtained in the mean PR may then be related to the amount and arrangement of collagen and cells in the cardiac tissue.

In some aspects, an inflection point in the slope of the phase retardation data may be identified a few hundred microns after the tissue surface. This depth may correspond with a transition between endocardium (collagen) and myocardium (mainly cardiomyocytes) in the tissue. The mean PR slope, $R^2$ value, root mean square error (RMSE) value, and the ratio between the maximum and minimum PR calculated from the end of the estimation of the endocardial wall to the maximum value may be associated with the arrangement of cardiomyocytes in the myocardium.

In some aspects, a histological analysis of the tissue (e.g., using staining techniques) may be performed to correlate the polarization-sensitive optical coherence reflectometry (PS-OCR) with the muscle fibers' arrangement in the tissue, such as to identify collagen and cardiomyocytes in the PS-OCR images and exclude any abnormal micro-anatomy from the measurements used in the linear regression model.

In some aspects, the $R^2$ value and the root mean square error (RMSE) associated with the linear regression model may be related to the cellular organization within the tissue, so small $R^2$ values (e.g., <0.8) or high RMSE values (e.g., >0.025) may indicate an excess of collagen in the extracellular matrix or a thick wall of endocardium, which may reduce cellular organization.

Figure 6:
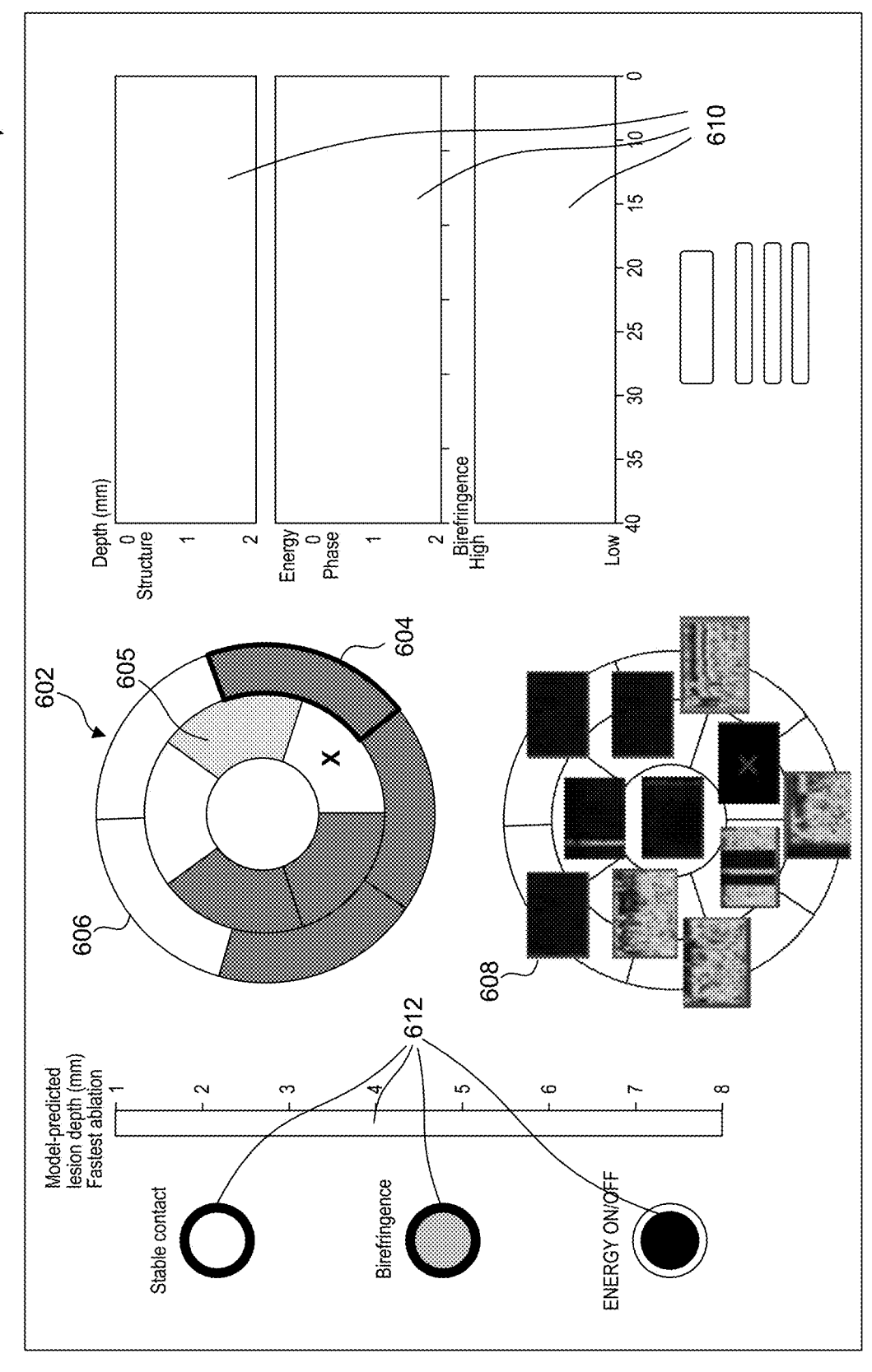
FIG. 6 shows a graphical user interface for displaying information acquired via optical inspection of a sample, according to some aspects.

FIG. 6 shows a GUI 600 showing predicted lesion depths, according to some aspects. In some aspects, the GUI 600 may be presented on display 325 coupled to console 310 (FIG. 3), in which optical measurement data may be obtained by optical system 401 (FIG. 4). GUI 600 may display optical measurement data, for example as processed by console 310 (FIG. 3), in real-time or near real-time for an ablation process. GUI 600 may display a front view 602 of the catheter tip showing different sections 604-606 corresponding to the various optical view ports of the catheter tip.

In some aspects, front view 602 may show which optical view ports of the catheter tip are in contact with tissue and which beams from the different optical view ports are in operation. For example, the dark gray sections 604 of the front view 602 may indicate a strong contact between the catheter and tissue, the light gray section 605 may indicate a minimal or intermediate contact between the catheter and tissue, and the white sections 606 may indicate no contact.

Sections 604-606 may also indicate which beams are switched on or off for obtaining optical measurements from the tissue. Dark gray sections 604 and light gray section 605 may indicate that the beams from the corresponding optical view ports are turned on, whereas the white sections 606 may indicate that the corresponding optical view ports are turned off. The color schemes described here are provided for the purposes of example and are not intended to be limiting. Indication of various characteristics of contact may be provided via any suitable visual indicators.

In some aspects, GUI 600 may show a plurality of indicators 608 for showing the optical readout of each optical view port section in the catheter. The plurality of indicators 608 may each correspond to the different sections 604-606. Each indicator 608 may present an image resulting from processing, by the console, an optical signal from an optical measurement obtained from a respective optical view port section in the catheter. Individual indicators 608 may be switched on or off (or may appear or disappear) based on a particular optical view port section being active at a given time.

In some aspects, GUI 600 may include one or more graphs 610 showing ablation energy data (e.g., RF or PFA power), birefringence data, phase data, and predicted lesion depth data. GUI 100 may include one or more panels or indicators 612 that show whether contact between the catheter tip and tissue is stable, loss in birefringence, status of the ablation energy (e.g., on/off), and predicted lesion depths. It is to be appreciated that elements of GUI 600 may be mixed, overlapped, or otherwise rearranged. For example, contact stability indicators may be worked into front view 602 and/or indicators 608. There may also be indicators for soft contact (mere touch of catheter to tissue) and/or hard contact (e.g., catheter contact causes indentation of tissue).

In some aspects, GUI 600 may include one or more buttons or text boxes that allow user selection and/or customization of parameters selected for ablation or for operating the catheter during ablation.

Other examples of optical measurements and GUI implementations may be found in U.S. Pub. Appl. No. 2021/0212569 (filed on Jan. 13, 2021), which is incorporated herein by reference in its entirety.

Example Catheter-to-Tissue Contact Analysis Based on Optical Measurement

In some aspects, the stability of catheter-to-tissue contact may greatly affect the success of an ablation attempt. The size and shape of the denaturated lesion volume of tissue may be affected by the stability of the contact between the catheter and the tissue. Conventional methods currently use a force sensor to measure the force applied by the catheter on the tissue. However, the information gained by this method may be very limited for the purposes of contact stability. For example, a force sensor may be limited in direction (e.g., unidirectional). A force measurement in a beating heart may be highly dependent on filtering. A force measurement may be biased by the angle of incidence of the catheter on the target tissue. It is usually recommended to use the force sensor with a force of 15 grams to 20 grams during the ablation, but it may be the physician that ultimately makes a judgement on whether a contact is stable or not (e.g., possible human error).

In some aspects, data from optical measurements (e.g., birefringence data) may be analyzed in order to make a determination of stability of contact between catheter and tissue. In this manner, the use of force sensors and their drawbacks may be avoided or relegated to provide secondary confirmation.

Figure 7B:
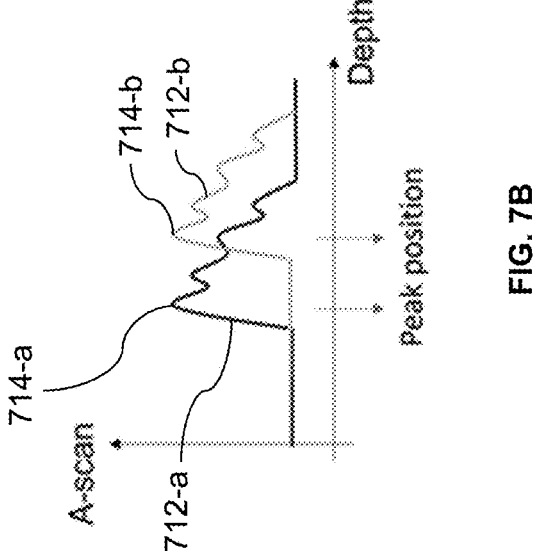
FIG. 7B shows A-scan graphs that correspond to the catheter configurations shown in FIG. 7A, according to some aspects.
Figure 7A:
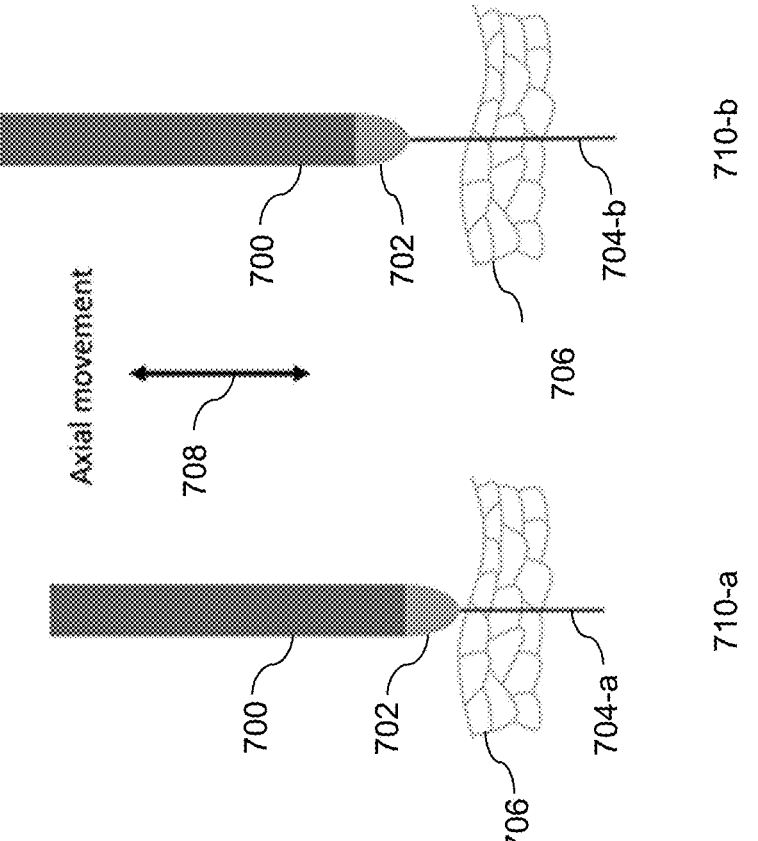
FIG. 7A shows a catheter in different configurations with respect to a target tissue, according to some aspects.

FIG. 7A shows a catheter 700 disposed at different distances from a target tissue 706, according to some aspects. FIG. 7B shows a graph with data corresponding to the different positions of catheter 700, according to some aspects. In some aspects, catheter 700 may correspond to other catheters disclosed herein (e.g., catheters 100, 302 (FIGS. 1, 3)) and be used in connection with systems disclosed herein (e.g., systems 300, 401 (FIGS. 3, 4)).

In some aspects, catheter 700 may be moved along an optical axis, denoted by axial direction 708 (e.g., toward or away from target tissue 706, as opposed to a lateral direction that is perpendicular to axial direction 708). Movement along axial direction 708 may be referred to as axial movement of catheter 700. Catheter 702 may comprise a distal portion 702 that may come into contact with target tissue 706.

In some aspects, of the two catheter configurations shown in FIG. 7A, the configuration on the left may be referred to as configuration 710-a. Configuration 710-a corresponds to catheter 700 being closer to, or in contact with, target tissue 706 (e.g., disposed at a first position). In contrast, the configuration on the right (configuration 710-b) may correspond to catheter 700 being disposed at a further distance from target tissue 706 (e.g., disposed at a second position). The suffixes "a" and "b" used in the reference numerals are used to denote correspondence to either configuration 710-a or 710-b.

In some aspects, illumination 704-a may represent illumination that has been scattered by target tissue 706 while the catheter is disposed at a first position relative to target tissue 706. Illumination 704-b may represent illumination that has been scattered by target tissue 706 while the catheter is disposed at a second position relative to target tissue 706. The scattered illumination may be received at a detection system in system 401 (FIG. 4), which then generates corresponding measurement signals to be analyzed by processing device 108 (FIG. 1). Plotline 712-a in FIG. 7B may be a graphical representation of a measurement signal associated with configuration 710-a (e.g., a first measurement signal). Plotline 712-b in FIG. 7B may be a graphical representation of a measurement signal associated with configuration 710-b (e.g., a second measurement signals). The vertical axis of the plot may represent a characteristic of an A-scan (e.g., signal intensity, signal phase, or the like). The horizontal axis of the plot may represent a distance (e.g., depth as measured relative to catheter tip). A plurality of measurement signals may be generated according to other configurations (e.g., first, second, third, and so on, measurement signals).

In some aspects, the data represented by plotline 712-a may comprise an identifiable characteristic, for example, illustrated as a feature 714-a (e.g., a maximum, a minimum, an inflection, or the like). Here, the feature is depicted as a peak. Similarly, feature 714-b corresponds to plotline 712-b. While these are graphical representations of features and data, it is to be understood that such features and data may be available in various forms. For example, the identifiable characteristics may be present in the electromagnetic form of the measurement signals (e.g., highs and lows of intensity or phase shift), in digital values as interpreted by processing device 108 (FIG. 1), or the like.

In some aspects, the peak position of the plotline may shift, as shown in FIG. 7B, as a result of the motion of catheter 700 along optical axis 708, shown in FIG. 7A. The shifting of the plotline represents a difference between a plurality of measurement signals (e.g., a difference between first and second measurement signals). For example, as catheter 700 moves closer to target tissue 706 (e.g., from the position shown in configuration 710-*b* to the position shown in configuration 710-*a*), the corresponding plotline in FIG. 7B shifts in location from right to left (e.g., from plotline 712-*b* to plotline 712-*a*). The opposite would occur as the catheter moves away from target tissue 706. This signal shift may be observed in real-time as catheter 700 moves, indicating that catheter 700 indeed is moving relative to the target tissue, and thus not in contact with the target tissue.

However, when catheter 700 makes contact with target tissue 706, any further movement of catheter 700 toward target tissue 706 merely pushes against the surface of tissue target 706 (i.e., the relative position of catheter 700 and the surface of target tissue 706 is unchanged). The result is that the shifting of plotline 712-*a*/712-*b* may stabilize or stop (e.g., the difference between the plurality of measurement signals shrinks or vanishes). In other words, determining whether a viewport of catheter 700 is in contact with target tissue 706 may be based on a difference between the plurality of optical measurements meeting or crossing a threshold value. In this manner, the determining of whether a viewport of catheter 700 is in contact with target tissue 706 may be independent of a contact force measurement.

In some aspects, it may also be useful to assess a stability of the contact between catheter 700 and target tissue 706. To assess stability, additional optical measurements may be analyzed. For example, processing device 108 (FIG. 1) may analyze three or more optical measurements. Determination of contact may be performed as described above by analyzing a first difference, the first difference being with respect to first and second optical measurements (e.g., little to no difference, such as difference at or below a predetermined threshold, is associated with contact=true). Determination of contact may also be performed by analyzing a second difference, the second difference being with respect to second and third optical measurements. If the first and second differences are both evaluated as contact=true, then system 300 (FIG. 3) may display an indication that contact between catheter 700 and target tissue 706 is stable. Processing device 108 may provide an indication of stability when catheter 700 is continuously in contact with target tissue 706, but provide an indication of instability when catheter 700 is intermittently in contact with target tissue 706. For example, processing device 108 may cause an audio signal to sound as real-time feedback, and/or processing device 108 may cause a graphical user interface to output a visual indicator of contact stability, such as discussed with respect to FIG. 6.

Figure 8B:
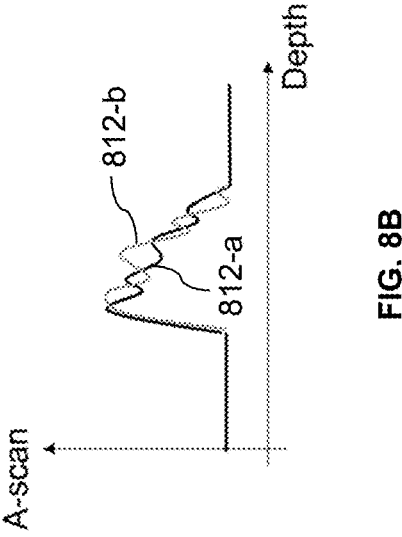
FIG. 8B shows A-scan graphs that correspond to the catheter configurations shown in FIG. 8A, according to some aspects.
Figure 8A:
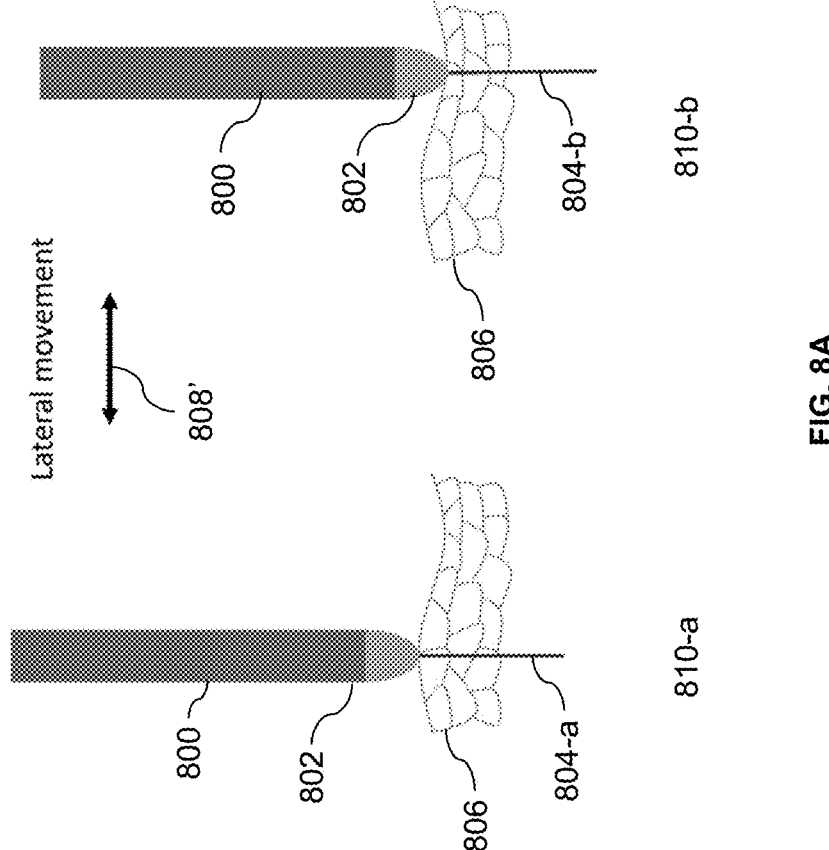
FIG. 8A shows a catheter in different configurations with respect to a target tissue, according to some aspects.

FIG. 8A shows a catheter 800 disposed at different locations along the surface of a target tissue 806, according to some aspects. FIG. 8B shows a graph with data corresponding to the different positions of catheter 800, according to some aspects. In some aspects, catheter 800 may correspond to other catheters disclosed herein (e.g., catheters 100, 302, 700 (FIGS. 1, 3, 7)) and be used in connection with systems disclosed herein (e.g., systems 300, 401 (FIGS. 3, 4)). Whereas FIG. 7A illustrated catheter motion along axial direction 708, FIG. 8A illustrates a lateral motion (e.g., motion generally perpendicular to the optical axis) of catheter 800. One of skill in the art will appreciate that such lateral movement may include any movement along the surface of the tissue, not strictly linear motion.

In some aspects, elements that may be duplicative between FIGS. 7A/7B and 8A/8B may have reference numbers that share the two right-most numeric digits. Such elements may include, for example, catheter 800, distal portion 802, illumination 804-*a*, illumination 804-*b*, target tissue 806, configuration 810-*a*, configuration 810-*b*, plotline 812-*a*, and plotline 812-*b*. The structures, functions, and/or characteristics of these elements may be inferred from descriptions of FIG. 7A/7B. It is to be appreciated that some differences between elements of FIGS. 7A/7B and 8A/8B may be attributed to differences in direction of motion of the catheter.

In some aspects, lateral direction 808' may be perpendicular to axial direction 708 (FIG. 7A). A first optical measurement may be performed using catheter 800 at a first position of the surface of tissue 806 (configuration 810-*a*). A first portion of target tissue 806 at the first position may have a first structure. The measurement signal that corresponds to the first portion of target tissue 806 may be represented by plotline 812-*a* in FIG. 8B. That is, plotline 812-*a* may represent a signature of the measurement signal resulting from catheter configuration 810-*a* in FIG. 8A. The signature may comprise the magnitude profile as a function of depth (e.g., distance from the viewport) as depicted by plotline 812-*a*. When catheter 800 is moved to a second position (configuration 810-*b* in FIG. 8A), the measurement signal may have changed so as to be represented by plotline 812-*b* in FIG. 8B, which corresponds to a second portion of target tissue 806 at the second position (the tissue structure here may be a second tissue structure). In contrast to the axial motion of FIG. 7A (e.g., peak shift with respect to depth shown in FIG. 7B), the differences in the measurement signals corresponding to plotlines 812-*a* and 812-*b* may be more dependent on structural differences between the first and second portions of target tissue 806.

For example, in some aspects, a processing device may analyze the measurement signals for differences such as creation, disappearance, and/or changes in magnitude of features (such features may include, for example, maximum/a, minimum/a, inflection(s), rising edge, falling edge, or the like). In other words, the processing device may evaluate whether the magnitude profiles of the measurements have changed between optical measurements. It is to be appreciated that magnitude profiles may have more than one type of representation. For example, plotlines 812-*a* and 812-*b* are graphical representations. The analog form of a measurement signal may convey an electromagnetic representation of a magnitude profile. A processing device may convert the electromagnetic representation into a digital representation.

FIGS. 8A and 8B thus illustrate that, as catheter 800 laterally shifts along the surface of target tissue 806 (e.g., from position 804-*a* to position 804-*b*), the profile (e.g., shape) of the resultant optical signal also shifts (e.g., from plotline 812-*a* to plotline 812-*b*). This signal shift may be observed in real-time as catheter 800 moves, indicating that catheter 800 indeed is moving relative to the target tissue, and thus not stably contact with the target tissue. However, when catheter 800 reduces or stops moving, the shifting between plotlines 812-*a* and 812-*b* may also stabilize or stop (e.g., the difference between successive measurement signals shrinks or vanishes). In other words, determining whether a viewport of catheter 800 is in stable contact with target tissue 806, such that lateral movement is minimal or nonexistent, may be based on a difference between the plurality of optical measurements in successive plotlines 812-*a* and 812-*b* meeting or crossing a threshold value.

In some aspects, determination of contact and contact stability using lateral motion of the catheter may be used on its own or may be combined with methods described above for axial motion of the catheter.

Figure 9:
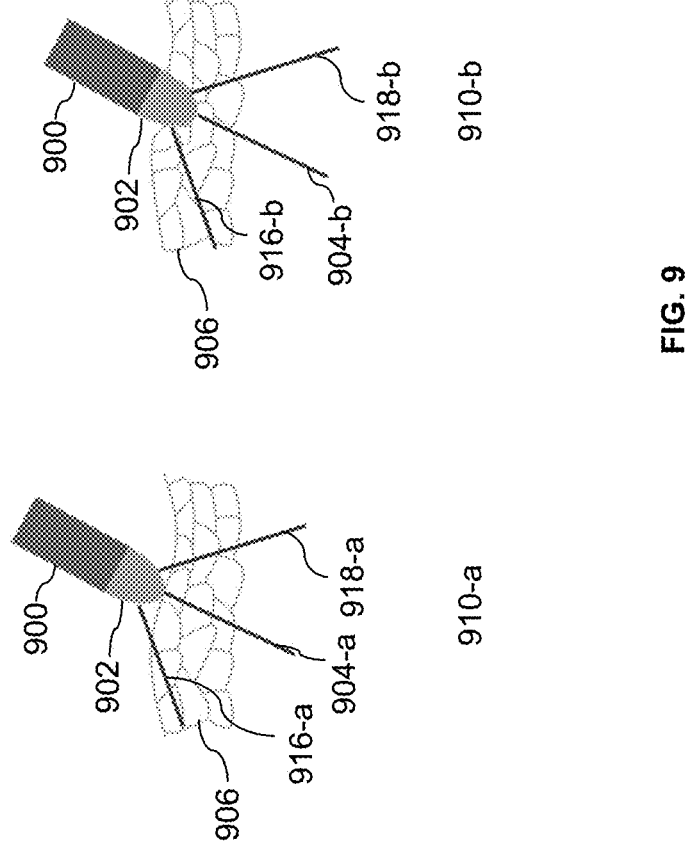
FIG. 9 shows a catheter in different configurations with respect to a target tissue, according to some aspects.

FIG. 9 shows a catheter 900 disposed at different distances from a target tissue 906, according to some aspects. In some aspects, catheter 900 may correspond to other catheters disclosed herein (e.g., catheters 100, 302, 700, 800 (FIGS. 1, 3, 7, 8)) and be used in connection with systems disclosed herein (e.g., systems 300, 401 (FIGS. 3, 4)). Whereas FIGS. 7A and 8A illustrated single viewport contact, FIG. 9 illustrates multiple viewports of catheter 900 in contact with target tissue 906.

In some aspects, elements that may be duplicative between FIGS. 7A, 8A, and 9 may have reference numbers that share the two right-most numeric digits. Such elements may include, for example, catheter 900, distal portion 902, illumination 904-a, illumination 904-b, target tissue 906, configuration 910-a, and configuration 910-b. The structures, functions, and/or characteristics of these elements may be inferred from descriptions of FIGS. 7A and 8A. It is to be appreciated that some differences between elements of FIGS. 7A, 8A, and 9 may be attributed to differences in the motion of the catheter.

In some aspects, configuration 910-a may correspond to an arrangement in which a single viewport of catheter 900 is in contact with target tissue 906. Illumination 904-a may correspond to a viewport at a tip of distal portion 902, and this viewport is in contact with target tissue 906 (contact=true). Illumination 904-a may be, in this example, parallel to an optical axis of distal portion 902 (e.g., looking straight ahead). Illumination 916-a and 918-a may correspond to other viewports directed at different angles with respect to the optical axis of distal section 902. Illumination 916-a and 918-a may correspond to measurement signals that are interpreted by processing device 108 (FIG. 1) as contact=false. In this scenario of a single viewport being in contact with target tissue 906, system 300 (FIG. 3) may indicate to a user that catheter 900 is in soft contact with target tissue 906.

In some aspects, configuration 910-b may correspond to an arrangement in which multiple viewports of catheter 900 are in contact with target tissue 906. That is, catheter 900 has been moved toward target tissue 906 such that distal portion 902 creates an indentation in target tissue 906. Illumination 904-b, 916-b and 918-b may correspond to measurement signals that are interpreted by processing device 108 (FIG. 1) as contact=true. In this scenario of multiple viewports being in contact, system 300 (FIG. 3) may indicate to a user that catheter 900 is in hard contact with target tissue 906. A skilled artisan will appreciate that different definitions of soft contact and hard contact may be used (e.g., soft contact=2 or fewer ports in contact while hard contact=3 or more ports in contact).

In some aspects, the determination of contact, determination of stable contact, and/or determination of soft/hard contact may be displayed via GUI 600 (FIG. 6) on display 325 (FIG. 3).

The catheters, consoles, and systems described herein may be used to perform optical analysis and lesion depth prediction of tissue. By utilizing the optical analysis and lesion prediction methods described herein, the catheter and optical systems disclosed herein (e.g., catheter system 300 and optical system 401) may allow evaluation of a lesion formation in tissue in or near real-time, with accuracy, sensitivity and specificity values above 90% (e.g., 93.5%, 92.9% and 96.6%, respectively).

Example Method of Operation

Various methods and other aspects of catheters and systems described thus far may be implemented, for example, using catheter 100 shown in FIG. 1, system 300 shown in FIG. 3 (including catheter 302 and console 310), optical system 401 shown in FIG. 4, and the aspects shown in FIGS. 5-9.

FIG. 10 shows a method 1000 for determining characteristics of contact between a catheter and a target tissue, according to some aspects. In some aspects, a plurality of optical measurements of a target tissue may be performed via a viewport disposed at a distal end of a catheter. The performing of the plurality of the optical measurements may comprise steps S1002, S1004, S1006, S1008, and S1010. The plurality of optical measurements may then be analyzed as described in step S1012.

In some aspects, at step S1002, illumination may be transmitted toward the target tissue via the viewport. The illumination may be provided in discrete time frames (e.g., pulses). The illumination may be scattered and reflected by the target tissue back toward the viewport. The viewport may be one of a plurality of viewports of a catheter. The viewport may be disposed at a distal portion of the catheter. At step S1004, first scattered illumination from the target tissue may be received via the viewport. At step S1006, a first measurement signal may be generated, by a detection system, based on the receiving of the first scattered illumination. At step S1008, second scattered illumination from the target tissue may be received via the viewport. At step S1010, a second measurement signal may be generated, by the detection system, based on the receiving of the second scattered illumination.

In some aspects, a first optical measurement may comprise steps S1004 and S1006 and a second optical measurement may comprise steps S1008 and S1010. Such steps may be repeated to perform a third optical measurement, a fourth optical measurement, and the like. In some aspects, steps S1106 and S1010 may be performed by a signal processor, such as processing device 108.

In some aspects, at step S1012, a processing device, such as processing device 108, may determine whether the viewport is in contact with the target tissue based on a first difference among the plurality of optical measurements meeting or crossing a first threshold value. In some aspects, the first difference may comprise a difference between the first and second measurement signals. In one non-limiting example, the first difference may correspond to a shift in an identifiable feature in the first and second measurement signals (e.g., a shift in a maximum intensity, such as the shift between features 714-a and 714-b (FIG. 7B)). Or the first difference may correspond to a difference in the structure of the first and second measurement signals (alluding to FIG. 8B and lateral motion of the catheter). For example, the first measurement signal may comprise first data features (e.g., minimum/a, maximum/a, or the like) and the second measurement signal may comprise second data features. The first data features may act as a signature of the first scattered illumination and the second data features may act as a signature of the second scattered illumination. The difference between the first and second measurement signals may be evaluated based on a difference between the signatures of the first and second scattered illumination (may also be referred to as an A-scan differential measurement).

In some aspects, both axial movement and lateral movement are determined from the same first and second measurement signals. For example, shifting of a location along the axis of a notable feature between the first and second measurement signals may be used to determine axial contact and/or contact stability, as discussed with respect to FIGS. 7A and 7B, while changes between the profiles of the first and second measurement signals may be used to determine lateral contact stability, as discussed with respect to FIGS. 8A and 8B. A determination of contact stability can thus be based on an evaluation of both axial and lateral movement together, axial movement alone, or lateral movement alone.

In some aspects, the previously mentioned threshold value may be implemented to prevent oversensitivity of the system. In a non-limiting example, when the catheter is not in contact with the target tissue, the system may be programmed to expect a change of a feature in the measurement signals (e.g., expect a shift a peak in the data as described in reference to FIG. 7B). The expected change in the measurement signals may form the basis for a threshold value. The catheter may be moved and, if the measured difference in measurement signals meets or crosses the threshold condition (e.g., at or greater than the threshold value), the system may evaluate that the catheter is not in contact with the target tissue. Conversely, if the catheter is moved and the measured difference in measurement signals meets or crosses an opposing threshold condition (e.g., below the threshold), the system may evaluate that the catheter is in contact with the target tissue. It is to be appreciated that threshold values and conditions may be defined in a number of suitable ways evident to a skilled artisan to achieve the contact analyses described herein.

The method steps of FIG. 10 may be performed in any conceivable order and it is not required that all steps be performed. Moreover, the method steps of FIG. 10 described above merely reflect an example of steps and are not limiting. That is, further method steps and functions may be envisaged based upon embodiments described in reference to FIGS. 1-9. For example, the method may further comprise displaying, at a graphical user interface, an indication of whether the viewport is in contact with the target tissue, an indication of whether a contact between the viewport and the target tissue is stable, and/or an indication of whether the contact is a soft contact or a hard contact. The method may also comprise determining whether the contact is a soft or hard contact by using data collected from multiple viewports (as described in reference to FIG. 9).

Example Computer System

Figure 11:
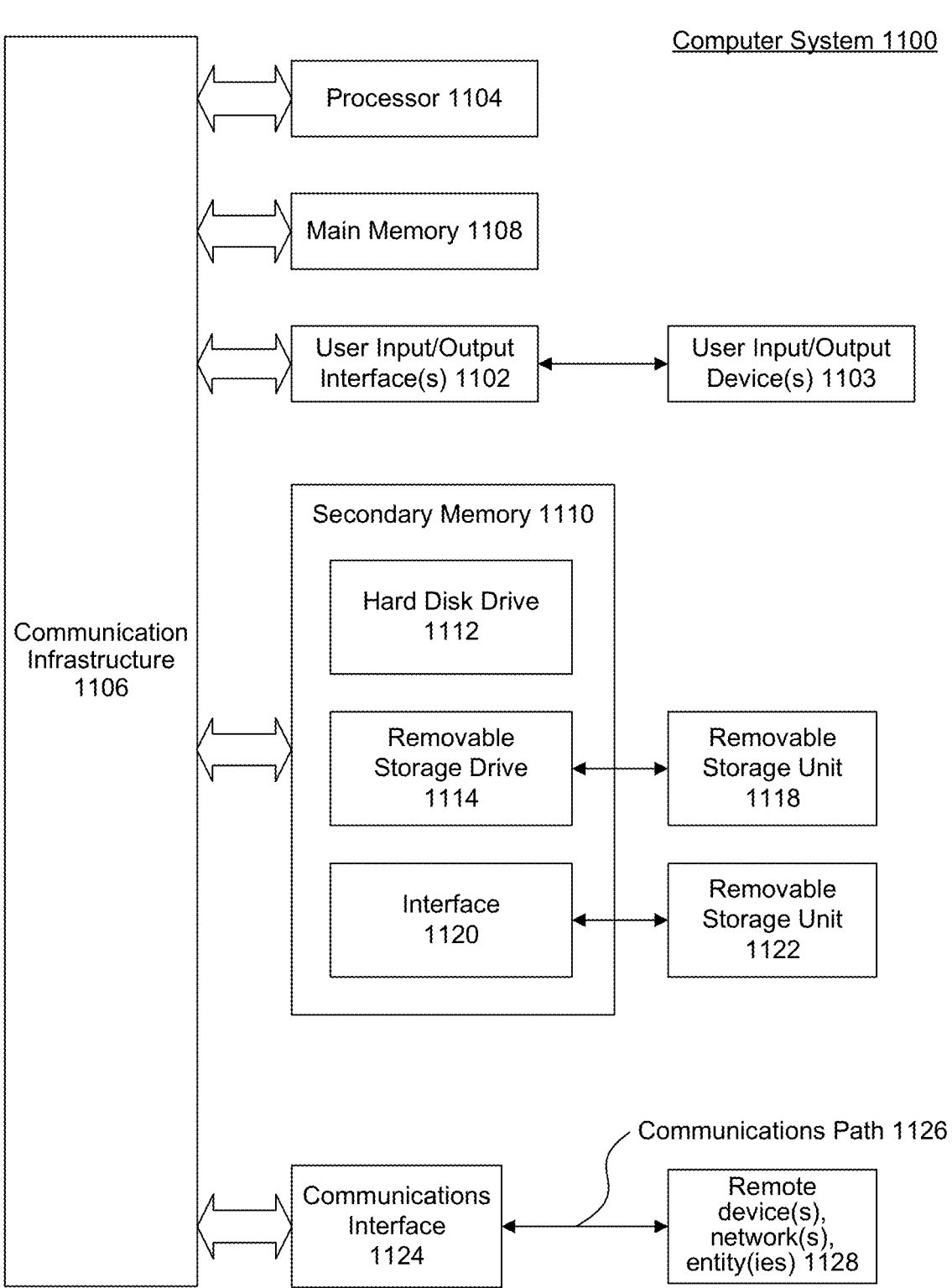
FIG. 11 shows a computer system, according to some aspects.

FIG. 11 is a block diagram of example components of computer system 1100. One or more computer systems 1100 may be used, for example, to implement any of the aspects discussed herein, as well as combinations and sub-combinations thereof. In some aspects, one or more computer systems 1100 may be used to implement method 1000 shown in FIG. 10, and/or processing device 108, console 310, signal generator 320, and/or display 325, as described herein. Computer system 1100 may include one or more processors (also called central processing units, or CPUs), such as a processor 1104. Processor 1104 may be connected to a communication infrastructure or bus 1106.

In some aspects, computer system 1100 may also include user input/output interface(s) 1102, such as monitors, keyboards, pointing devices, etc., which may communicate with communication infrastructure 1106 through user input/output interface(s) 1103.

In some aspects, one or more of processors 1104 may be a graphics processing unit (GPU). A GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

In some aspects, computer system 1100 may also include a main or primary memory 1108, such as random access memory (RAM). Main memory 1108 may include one or more levels of cache. Main memory 1108 may have stored therein control logic (i.e., computer software) and/or data. In some aspects, main memory 1108 may include optical logic configured to perform analysis of optical measurements obtained from tissue by a catheter and determine lesion predictions.

In some aspects, computer system 1100 may also include one or more secondary storage devices or memory 1110. Secondary memory 1110 may include, for example, a hard disk drive 1112 and/or a removable storage drive 1114.

In some aspects, removable storage drive 1114 may interact with a removable storage unit 1118. Removable storage unit 1118 may include a computer usable or readable storage device having stored thereon computer software (control logic) and/or data. Removable storage unit 1118 may be a program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 1114 may read from and/or write to removable storage unit 1118.

In some aspects, secondary memory 1110 may include other means, devices, components, instrumentalities or other approaches for allowing computer programs and/or other instructions and/or data to be accessed by computer system 1100. Such means, devices, components, instrumentalities or other approaches may include, for example, a removable storage unit 1122 and an interface 1120. Examples of the removable storage unit 1122 and the interface 1120 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

In some aspects, computer system 1100 may further include a communication or network interface 1124. Communication interface 1124 may allow computer system 1100 to communicate and interact with any combination of external devices, external networks, external entities, etc. (individually and collectively referenced by reference number 1128). For example, communication interface 1124 may allow computer system 1100 to communicate with external or remote devices 1128 over communications path 1126, which may be wired and/or wireless (or a combination thereof), and which may include any combination of LANs, WANs, the Internet, etc. Control logic and/or data may be transmitted to and from computer system 1100 via communication path 1126. Computer system 1100 may be coupled to a catheter via a connector and optical and electrical connections at communication interface 1124, including optical fibers and electrical wiring, pins, and/or components.

In some aspects, computer system 1100 may also be any of a personal digital assistant (PDA), desktop workstation, laptop or notebook computer, netbook, tablet, smartphone, smartwatch or other wearables, appliance, part of the Internet-of-Things, and/or embedded system, to name a few non-limiting examples, or any combination thereof.

In some aspects, computer system 1100 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

In some aspects, any applicable data structures, file formats, and schemas in computer system 1100 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some aspects, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1100, main memory 1108, secondary memory 1110, and removable storage units 1118 and 1122, as well as tangible articles of manufacture embodying any combination of the foregoing. Such control logic, when executed by one or more data processing devices (such as computer system 1100), may cause such data processing devices to operate as described herein.

It is to be appreciated that the Detailed Description section, and not the Summary and Abstract sections, is intended to be used to interpret the claims. The Summary and Abstract sections may set forth one or more but not all example aspects of the present disclosure as contemplated by the inventor(s), and thus, are not intended to limit the present disclosure and the appended claims in any way.

Aspects of the present disclosure have been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described example aspects, but should be defined only in accordance with the following claims and their equivalents.

Furthermore, the following aspects are explicitly disclosed in the following clauses:

1. A method comprising:
performing a plurality of optical measurements of a target tissue via a viewport disposed at a distal portion of a catheter, the performing comprising:
transmitting illumination toward a target tissue via the viewport;
receiving, at the viewport, first scattered illumination from the target tissue;
generating a first measurement signal based on the first scattered illumination;
receiving, at the viewport, second scattered illumination from the target tissue after the receiving of the first scattered illumination; and
generating a second measurement signal based on the second scattered illumination; and
analyzing the plurality of optical measurements, the analyzing comprising:
determining whether the viewport is in contact with the target tissue based on a first difference among the plurality of optical measurements meeting or crossing a first threshold value, wherein the first difference comprises a difference between the first and second measurement signals.

2. The method of aspect 1, wherein the determining of whether the viewport is in contact with the target is independent of a contact force measurement.

3. The method of aspect 1 or aspect 2, wherein:
the performing of the plurality of optical measurements further comprises:
receiving, at the viewport, a third scattered illumination from the target tissue after the receiving of the second scattered illumination; and
generating a third measurement signal based on the third scattered illumination; and
the analyzing further comprises:
determining whether a contact between the viewport and the target tissue is stable based on the first difference and a second difference among the plurality of optical measurements meeting or crossing a second threshold value, the second difference comprising a difference between the second and third measurement signals.

4. The method of aspect 3, wherein the determining of whether the contact is stable is independent of a contact force measurement.

5. The method of any of aspects 1-4, wherein:
the first and second measurement signals comprise data of scattered illumination intensity as a function of distance from the viewport; and
the difference between the first and second measurement signals is evaluated based on a shift of the scattered illumination intensity with respect to the distance from the viewport.

6. The method of any of aspects 1-5, wherein:
the first measurement signal comprises a first magnitude profile as a function of distance from the viewport;
the second measurement signal comprises a second magnitude profile as a function of distance from the first viewport; and
the difference between the first and second measurement signals is based on a difference between the first and second magnitude profiles.

7. The method of any of aspects 1-6, wherein the viewport is a first viewport and the method further comprises:

performing a plurality of optical measurements of the target tissue via a second viewport disposed at the distal portion of the catheter;

determining whether the second viewport is in contact with the target tissue based on the plurality of optical measurements of the target tissue via the second viewport; and determining whether the distal portion of the catheter is in soft or hard contact with the target tissue based on the determining of whether the first and second viewports are in contact with the target tissue, wherein hard contact is associated with two or more viewports being in contact with the target tissue.

8. The method of any of aspects 1-6, further comprising displaying, at a graphical user interface, an indication of whether the viewport is in contact with the target tissue.

9 The method of any of aspects 3-8, further comprising displaying, at a graphical user interface, an indication of whether a contact between the viewport and the target tissue is stable.

10. The method of any of aspects 3-9, further comprising displaying, at a graphical user interface, an indication of whether the contact is a soft contact or a hard contact.

11. The method of any one of aspects 7-10, further comprising displaying, at a graphical user interface, whether the second viewport is in contact with the target tissue.

12. The method of any one of aspects 3-11, further comprising displaying, at a graphical user interface, birefringence data, phase data, and/or lesion depth data.

13. A system comprising:

a catheter comprising
  a proximal portion;
  a distal portion:
  a sheath coupled between the proximal section and the distal section; and
  a plurality of viewports disposed at the distal portion and configured to transmit illumination to a target tissue and to receive scattered illumination from the target tissue;

a detection system configured to receive, via a first viewport of the plurality of viewports, first and second scattered illumination from the target tissue and to generate first and second measurement signals respectively based on the first and second scattered illumination; and a processing device configured to determine whether the first viewport is in contact with the target tissue based on a first difference between the first and second measurement signals meeting or crossing a first threshold value.

14. The system of aspects 13, wherein the processing device is further configured to perform the determining of whether the first viewport is in contact with the target independent of a contact force measurement.

15. The system of aspect 13 or aspect 14, wherein:

the detection system is further configured to receive, via the first viewport, third scattered illumination from the target tissue and to generate a third measurement signal based on the third scattered illumination; and the processing device is further configured to determine whether a contact between the first viewport and the target tissue is stable based on the first difference and a second difference between the second and third measurement signals meeting or crossing a second threshold value.

16. The system of aspect 15, wherein the processing device is further configured to perform the determining of whether a contact between the first viewport and the target tissue is stable independent of a contact force measurement.

17. The system of any of aspects 13-16, wherein the detection system is further configured to generate the first and second measurement signals comprising data of scattered illumination intensity with respect to distance from the first viewport; and the processing device is further configured to evaluate the difference between the first and second measurement signals based on a shift of the scattered illumination intensity with respect to the distance from the first viewport.

18. The system of any of aspects 13-17, wherein:

the first measurement signal comprises a first magnitude profile as a function of distance from the first viewport;

the second measurement signal comprises a second magnitude profile as a function of distance from the first viewport; and the difference between the first and second measurement signals is based on a difference between the first and second magnitude profiles.

19. The system of any of aspects 13-18, wherein:

the detection system is further configured to receive, via a second viewport of the plurality of viewports, third and fourth scattered illumination from the target tissue and to generate third and fourth measurement signals respectively based on the third and fourth scattered illumination; and the processing device is further configured to:
  determine whether the second viewport is in contact with the target tissue based on an analysis of the third and fourth measurement signals; and
  determine whether the distal portion of the catheter is in soft or hard contact with the target tissue based on the determining of whether the first and second viewports are in contact with the target tissue, wherein hard contact is associated with two or more viewports being in contact with the target tissue.

20 The system of any of aspects 13-19, further comprising a display device configured to display, via a graphical user interface, an indication of whether the first viewport is in contact with the target tissue.

21 The system of any of aspects 15-20, wherein the display device is further configured to display, via the graphical user interface, an indication of whether a contact between the viewport and the target tissue is stable.

22. The system of any of aspects 15-21, wherein the display device is further configured to display, via the graphical user interface, an indication of whether the contact is a soft contact or a hard contact.

23. The system of any of aspects 19-22, wherein the display device is further configured to display, via the graphical user interface, whether the second viewport is in contact with the target tissue.

24. The system of any of aspects 15-23, wherein the display device is further configured to display, via the graphical user interface, birefringence data, phase data, and/or lesion depth data.

What is claimed is:

1. A method, comprising:
performing a plurality of optical measurements of a target tissue via a viewport disposed at a distal portion of a catheter, the performing comprising:
    transmitting illumination toward a target tissue via the viewport;
    receiving, at the viewport, first scattered illumination from the target tissue;
    generating a first measurement signal based on the first scattered illumination;
    receiving, at the viewport, second scattered illumination from the target tissue after the receiving of the first scattered illumination; and
    generating a second measurement signal based on the second scattered illumination; and
analyzing the plurality of optical measurements, the analyzing comprising:
    determining whether the viewport is in contact with the target tissue based on a first difference among the plurality of optical measurements meeting or crossing a first threshold value, wherein the first difference comprises a difference between the first and second measurement signals.

2. The method of claim 1, wherein the determining of whether the viewport is in contact with the target tissue is independent of a contact force measurement.

3. The method of claim 1, wherein:
the performing of the plurality of optical measurements further comprises:
    receiving, at the viewport, a third scattered illumination from the target tissue after the receiving of the second scattered illumination; and
    generating a third measurement signal based on the third scattered illumination; and
the analyzing further comprises:
    determining whether a contact between the viewport and the target tissue is stable based on the first difference and a second difference among the plurality of optical measurements meeting or crossing a second threshold value, the second difference comprising a difference between the second and third measurement signals.

4. The method of claim 3, wherein the determining of whether the contact is stable is independent of a contact force measurement.

5. The method of claim 1, wherein:
the first and second measurement signals comprise data of scattered illumination intensity as a function of distance from the viewport; and
the difference between the first and second measurement signals is evaluated based on a shift of the scattered illumination intensity with respect to the distance from the viewport.

6. The method of claim 1, wherein:
the first measurement signal comprises a first magnitude profile as a function of distance from the viewport;
the second measurement signal comprises a second magnitude profile as a function of distance from the viewport; and
the difference between the first and second measurement signals is based on a difference between the first and second magnitude profiles.

7. The method of claim 1, wherein the viewport is a first viewport and the method further comprises:

performing a plurality of optical measurements of the target tissue via a second viewport disposed at the distal portion of the catheter;
determining whether the second viewport is in contact with the target tissue based on the plurality of optical measurements of the target tissue via the second viewport; and
determining whether the distal portion of the catheter is in soft or hard contact with the target tissue based on the determining of whether the first and second viewports are in contact with the target tissue, wherein hard contact is associated with two or more viewports being in contact with the target tissue.

8. The method of claim 1, further comprising displaying, at a graphical user interface, an indication of whether the viewport is in contact with the target tissue.

9. The method of claim 3, further comprising displaying, at a graphical user interface, an indication of whether the contact between the viewport and the target tissue is stable.

10. The method of claim 3, further comprising displaying, at a graphical user interface, an indication of whether the contact between the viewport and the target tissue is a soft contact or a hard contact.

11. A system comprising:
a catheter comprising
    a proximal portion;
    a distal portion:
    a sheath coupled between the proximal portion and the distal portion; and
    a plurality of viewports disposed at the distal portion and configured to transmit illumination to a target tissue and to receive scattered illumination from the target tissue;
a detection system configured to receive, via a first viewport of the plurality of viewports, first and second scattered illumination from the target tissue and to generate first and second measurement signals respectively based on the first and second scattered illumination; and
a processing device configured to determine whether the first viewport is in contact with the target tissue based on a first difference between the first and second measurement signals meeting or crossing a first threshold value.

12. The system of claim 11, wherein the processing device is further configured to perform the determining of whether the first viewport is in contact with the target tissue independent of a contact force measurement.

13. The system of claim 11, wherein:
the detection system is further configured to receive, via the first viewport, third scattered illumination from the target tissue and to generate a third measurement signal based on the third scattered illumination; and
the processing device is further configured to determine whether a contact between the first viewport and the target tissue is stable based on the first difference and a second difference between the second and third measurement signals meeting or crossing a second threshold value.

14. The system of claim 13, wherein the processing device is further configured to perform the determining of whether a contact between the first viewport and the target tissue is stable independent of a contact force measurement.

15. The system of claim 11, wherein
the detection system is further configured to generate the first and second measurement signals comprising data of scattered illumination intensity with respect to distance from the first viewport; and the processing device is further configured to evaluate the first difference between the first and second measurement signals based on a shift of the scattered illumination intensity with respect to the distance from the first viewport.

16. The system of claim 11, wherein:

the first measurement signal comprises a first magnitude profile as a function of distance from the first viewport;

the second measurement signal comprises a second magnitude profile as a function of distance from the first viewport; and the first difference between the first and second measurement signals is based on a difference between the first and second magnitude profiles.

17. The system of claim 11, wherein:

the detection system is further configured to receive, via a second viewport of the plurality of viewports, third and fourth scattered illumination from the target tissue and to generate third and fourth measurement signals respectively based on the third and fourth scattered illumination; and the processing device is further configured to:

determine whether the second viewport is in contact with the target tissue based on an analysis of the third and fourth measurement signals; and determine whether the distal portion of the catheter is in soft or hard contact with the target tissue based on the determining of whether the first and second viewports are in contact with the target tissue, wherein hard contact is associated with two or more viewports being in contact with the target tissue.

18. The system of claim 11, further comprising a display device configured to display, via a graphical user interface, an indication of whether the first viewport is in contact with the target tissue.

19. The system of claim 18, wherein the display device is further configured to display, via the graphical user interface, whether a second viewport is in contact with the target tissue.

20. The system of claim 18, wherein the display device is further configured to display, via the graphical user interface, birefringence data, phase data, and/or lesion depth data.

* * * * *